United States Patent
Jeradechachai et al.

(10) Patent No.: US 11,802,838 B2
(45) Date of Patent: Oct. 31, 2023

(54) RAPID HIGH AMYLOSE WHEAT SEED PURITY TEST

(71) Applicant: BAY STATE MILLING COMPANY, Quincy, MA (US)

(72) Inventors: Tanya Jeradechachai, Platte City, MO (US); Sean Finnie, Quincy, MA (US); Alexis Schuko, Quincy, MA (US)

(73) Assignee: BAY STATE MILLING COMPANY, Quincy, MA (US)

( * ) Notice: Subject to any disclaimer, the term of this patent is extended or adjusted under 35 U.S.C. 154(b) by 263 days.

(21) Appl. No.: 17/301,056

(22) Filed: Mar. 23, 2021

(65) Prior Publication Data

US 2021/0293721 A1  Sep. 23, 2021

Related U.S. Application Data

(60) Provisional application No. 62/993,429, filed on Mar. 23, 2020.

(51) Int. Cl.
*G01N 21/78* (2006.01)
*G01N 1/28* (2006.01)
*G01N 1/40* (2006.01)

(52) U.S. Cl.
CPC .............. *G01N 21/78* (2013.01); *G01N 1/286* (2013.01); *G01N 1/4055* (2013.01); *G01N 2001/2866* (2013.01); *G01N 2001/2873* (2013.01); *G01N 2001/4061* (2013.01)

(58) Field of Classification Search
CPC ...... G01N 21/78; G01N 1/286; G01N 1/4055; G01N 2001/2866; G01N 2001/2873; G01N 2001/4061; G01N 33/0098; G01N 31/22; G01N 33/10
See application file for complete search history.

(56) References Cited

U.S. PATENT DOCUMENTS

| | | |
|---|---|---|
| 2,963,357 A | 11/1956 | Minto |
| 3,876,766 A | 4/1975 | Frommer et al. |
| 5,840,860 A | 11/1998 | Annison et al. |
| 6,825,342 B1 | 11/2004 | Cooke et al. |
| 7,919,132 B2 | 4/2011 | Regina et al. |
| 7,964,718 B2 | 6/2011 | Norman et al. |
| 7,998,888 B2 | 8/2011 | Shi et al. |
| 8,053,628 B2 | 11/2011 | Nakamura et al. |

(Continued)

FOREIGN PATENT DOCUMENTS

| | | | |
|---|---|---|---|
| CA | 2435053 A1 * | 1/2005 | ........... A23L 1/1812 |
| WO | 9104278 A1 | 4/1991 | |

(Continued)

*Primary Examiner* — Jennifer Wecker
*Assistant Examiner* — Ali Husain Faraz
(74) *Attorney, Agent, or Firm* — McKee, Voorhees & Sease, PLC

(57) ABSTRACT

Described herein are methods for quickly measuring properties of grain kernels. The methods allow for a quick, qualitative assessment of high amylose content in the grain kernel. The methods described herein allow for the assessment of high amylose content in wheat in either a laboratory setting or in the field with a minimum of equipment required. The results of these methods may be used to determine if high amylose kernels have been contaminated with normal or low amylose kernels.

19 Claims, 26 Drawing Sheets

(56) References Cited

U.S. PATENT DOCUMENTS

| | | |
|---|---|---|
| 8,110,677 B2 | 2/2012 | Zhang et al. |
| 8,115,087 B2 | 2/2012 | Regina et al. |
| 8,829,315 B2 | 9/2014 | Regina et al. |
| 9,212,351 B2 | 12/2015 | Li et al. |
| 10,301,637 B2 | 5/2019 | Clasen et al. |
| 2009/0011082 A1 | 1/2009 | Harris et al. |
| 2012/0309036 A1* | 12/2012 | Gubitz .................... C12Q 1/04 435/23 |
| 2013/0156924 A1 | 6/2013 | Morell et al. |
| 2017/0064986 A1 | 3/2017 | Regina et al. |
| 2017/0367382 A1 | 12/2017 | Regina et al. |
| 2018/0199607 A1 | 7/2018 | Kubota et al. |
| 2019/0338299 A1* | 11/2019 | Li .......................... A23L 7/197 |

FOREIGN PATENT DOCUMENTS

| | | |
|---|---|---|
| WO | 2018178121 A1 | 10/2018 |
| WO | 2019136518 A1 | 7/2019 |

\* cited by examiner

RAPID HIGH AMYLOSE WHEAT SEED PURITY TEST

FIELD OF THE INVENTION

This invention relates generally to methods for detecting kernels with a high amylose content. The methods may be used in a laboratory or field with minimal equipment and can be used to determine if high amylose kernels have been contaminated with normal or low amylose kernels.

CROSS REFERENCE

This application claims priority to and the benefit of U.S. Provisional Patent Application No. 62/933,429, filed Mar. 23, 2020, the above-identified application is incorporated by reference herein in its entirety.

BACKGROUND

High amylose wheat (greater than 60% amylose in the seed instead of the normal 20-30%) has desirable health benefits, however the trait can fluctuate with environmental or other conditions. Thus, testing needs to occur to understand purity of the seeds or the grain. Alternative tests to understand purity of the seeds with regard to amylose content include 1) Microscopy, 2) Single seed NIR, 3) Single seed amylose test. Microscopy involves the steps of grinding the individual seed then looking under microscope to see whether the seed is high amylose starch. This method takes a long time to grind each seed and look under microscope and throughput is low. The second method is single seed near infrared, which uses a single seed sorter with NIR, optical or other technology. Lastly, is the amylose method which includes starch extraction by grinding the sample and extracting starch. The starch is then purified by washing with water and centrifuging several times to collect the solids. It then dries overnight, and the starch is gelatinized by weighing out a known amount of starch and soaking in a water bath. The gelatinized starch is then mixed with iodine and water. Starch turns an intense blue-black color upon addition of aqueous solutions of the tri-iodide anion, due to the formation of an intermolecular change-transfer complex. In the absence of starch, the brown color of the aqueous solution remains. Once treated one can quantify the level of starch by using a spectrophotometer against known standard curve. This method is time consuming, 2-3 days.

For traditional seed testing, one needs to test 80-150 seeds per sample. The traditional laborious and time-consuming test is not practical. Thus, it can be seen that a need exists to quickly identify high amylose wheat and normal wheat.

BRIEF SUMMARY

Described herein is a rapid, qualitative kernel test that removes the step of amylose extraction and purification for determining amylose content of a sample of seeds. The process involves preparing the kernel to expose the starch contained within, then partial dissolution or dispersion of the amylose contained within the starch to gel the amylose, and then detecting the amylose concentration to differentiate between high amylose kernels and normal or low amylose kernels.

In an aspect the kernel is prepared to expose internal starch by cutting, crushing, or removing at least a portion of the bran. In some embodiments the kernel is cut. In a preferred embodiment, the kernel is cut in half. In other embodiments the kernel is cut into fourths. In other embodiments the bran layer is partially or entirely removed. In yet other embodiments the kernel is crushed.

After the starch is exposed, the starch may be at least partially dispersed or dissolved with a solvent. Due to the long linear chains of amylose and high intra and intermolecular hydrogen bonding, high amyloid starch is resistant to dissolution or dispersion. While dissolving, the hydrogen bonds and chains of amylose will engage more of the solvent and the crystalline structure of the starch will irreversibly disintegrates. Below a certain temperature, depending on the source of the amylose, the amylose will form a gel within a solvent as the linear chains force the solvent out of the chains in favor of aligning with itself or forming a double helix with other chains. Gelatinization of the amylose improves the availability of the amylose to other molecules or enzymes while maintaining the structure of the amylose chains. In an embodiment, the starch is dispersed into a colloidal dispersion in a solvent. In another embodiment, the starch is dissolved into the solvent. In an aspect, due to the helical structure of amylose and the hydrogen bonding, the dissolved or dispersed amylose will gel when cool.

In an aspect, the solvent used to disperse or dissolve the amylose will interact with the hydroxyl groups of the amylose chains to disperse or dissolve the amylose chains while maintaining the linear coil. In an embodiment the solvent is dimethyl sulfoxide (DMSO), urea in DMSO (UDMSO), iodine in DMSO ($I_2$DMSO), a Lewis base, an Arrhenius base, a halogen salt, or a strong acid. In a preferred embodiment, the solvent is basic. In a more preferred embodiment, the solvent is UDMSO. In another preferred embodiment, the solvent is KOH.

In an aspect the amount of solvent is used in a sufficient amount to submerge the prepared kernel. The amount of solvent will depend on the size of the kernel, the container the kernel is placed in for the reaction, and the boiling point of the solvent if heat is applied to the reaction. In an embodiment, the solvent is provided in about 150 μL to about 500 μL dissipating solvent. In a more preferred embodiment, the solvent is provided from about 175 μL to about 400 μL.

In some embodiments, a sufficient amount of time is allowed to pass to allow the solvent to dissolve or disperse part of the exposed starch into the solvent, allowing for the swelling and possible aggregation of amylose into a gel. In a preferred embodiment the sufficient amount of time is from about 10 seconds to about 15 minutes. In a more preferred embodiment the sufficient amount of time is from about 30 seconds to about 10 minutes. In an even more preferred embodiment the sufficient amount of time is from about 1 minute to about 5 minutes.

To aid in the swelling of the starch, in some embodiments, electromagnetic radiation is applied to add energy to the reaction to increase dispersion or dissolution of the amylose by aiding in breaking the hydrogen bonding within the amylose to allow the solvent to interact with the hydroxyl groups of the amylose. In a preferred embodiment, the electromagnetic radiation is microwave radiation and applied from about 1 second to about 90 seconds. In a more preferred embodiment the electromagnetic radiation is applied from about 10 to about 75 seconds. In an even more preferred embodiment, the radiation is applied from about 10 to about 60 seconds. After radiation is applied, the reaction is allowed to cool and the amylose will aggregate into a gel.

Various hydrophobic compounds may bind within an amylose coil, such as iodine, fatty acids, or aromatic compounds. In an embodiment, a detection molecule is added to the dissolved or dispersed amylose. In a preferred embodiment the dispersed or dissolved amylose is combined with iodine to produce a color. In an even more preferred embodiment, the source of iodine is potassium iodide iodine ($KI_2$). Due to iodine's instability in alkaline solutions, in embodiments in which a base is used to disperse or dissolve the amylose, it is preferable to neutralize the base prior to the addition of iodine.

The details of one or more embodiments of the invention are set forth in the accompanying drawings and the description below. Other features, objects, and advantages of the invention will be apparent from the description and drawings, and from the claims.

DETAILED DESCRIPTION

Figure 1A:
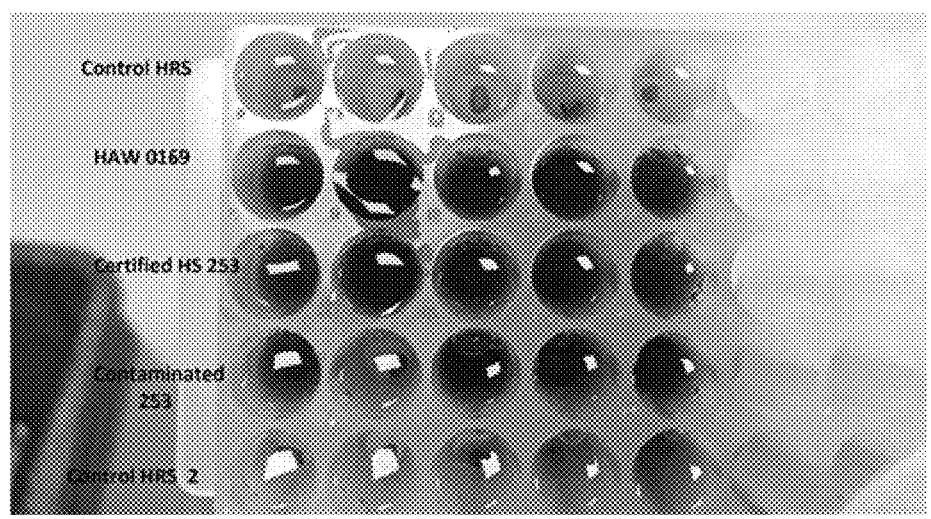
FIG. 1A shows an exemplary set up and results using the standard RAP on control and high amylose wheat.

So that the present invention may be more readily understood, certain terms are first defined. Unless defined otherwise, all technical and scientific terms used herein have the same meaning as commonly understood by one of ordinary skill in the art to which embodiments of the invention pertain. Many methods and materials similar, modified, or equivalent to those described herein can be used in the practice of the embodiments of the present invention without undue experimentation, the preferred materials and methods are described herein. In describing and claiming the embodiments of the present invention, the following terminology will be used in accordance with the definitions set out below.

The singular terms "a", "an", and "the" include plural referents unless context clearly indicates otherwise. Similarly, the word "or" is intended to include "and" unless the context clearly indicate otherwise. The word "or" means any one member of a particular list and also includes any combination of members of that list.

Numeric ranges recited within the specification, including ranges of "greater than," "at least," or "less than" a numeric value, are inclusive of the numbers defining the range and include each integer within the defined range.

The term "about," as used herein, refers to variation in the numerical quantity that can occur, for example, through typical measuring techniques and equipment, with respect to any quantifiable variable, including, but not limited to, mass, volume, time, distance, wavelength, frequency, voltage, current, and electromagnetic field. Further, given solid and liquid handling procedures used in the real world, there is certain inadvertent error and variation that is likely through differences in the manufacture, source, or purity of the ingredients used to make the compositions or carry out the methods and the like. The term "about" also encompasses amounts that differ due to different equilibrium conditions for a composition resulting from a particular initial mixture. The term "about" also encompasses these variations. Whether or not modified by the term "about," the claims include equivalents to the quantities.

As used herein, the term "grain" or "grain kernel" refers to small, hard, dried seeds with or without a hull or fruit layer. Exemplary types of grain include cereal grains, for example maize, corn, rice, soybeans, wheat, rye, millet, sorghum, barley, oats, rice, spelt, teff, fonio, triticale, amaranth, buckwheat, chia, *quinoa*, legumes, and oilseeds.

As used herein, the term "strong base" refers to a base which completely dissociates in water into the cation and the hydroxide ion and include the Arrhenius and Lewis bases. Arrhenius bases are alkali and alkaline earth metal hydroxides. Lewis bases react completely with water to deprotonate water leaving none of the original anion.

As used herein, the term "strong acid" refers to an acid which completely dissociates into their hydrogen ion and anion at 1.0 M or less. The strong acids are hydrochloric acid, nitric acid, sulfuric acid, hydrobromic acid, hydroiodic acid, perchloric acid, and chloric acid.

All publications, patents and patent applications identified herein are incorporated by reference, as though set forth herein in full. The invention being thus described, it will be apparent to those skilled in the art that the same may be varied in many ways without departing from the spirit and scope of the invention. Such variations are included within the scope of the following claims.

The invention is further illustrated by the following specific examples which are not intended in any way to limit the scope of the invention.

Kernel Preparation

The current protocols for amylose analysis include extracting the starch and then purifying the amylose within the starch. This extraction and purification is time consuming and limits the amount of samples that can be assayed in a day. Contrary to current protocols, disclosed herein is a rapid, qualitative method that does not need to extract the starch and then purify the amylose. Instead, the kernel is prepared by exposing the inner starch so that the amylose may be dissolved or dissipated by a solvent.

One skilled in the art will appreciate that the different grain kernels will have different sizes and different amylose content in the starch. Therefore, the different grain kernels will need to be prepared separately to expose a sufficient amount of starch. As used herein a "sufficient amount of starch" means that enough of the kernels starch is exposed for gelatinization to produce qualitative differences in coloration between high amylose and a normal or low amylose kernels without having to extract, purify, and/or dry the starch from kernel.

In some embodiments, the kernel is left whole with the bran layer partially removed. In a more preferred embodiment, the kernel is cut in half, in quarters, or in eighths. In other embodiments, for example naturally high amylose containing kernels like corn, the kernel may be portioned so that about 0.1%, about 1%, about 5%, about 10%, or more of the kernel is used for gelatinization. In other embodiments for naturally low amylose containing kernels, about 60%, about 70%, about 75%, about 80%, or more of the kernel may be used for gelatinization. In other embodiments, the whole or a portion of the kernel may be crushed prior to gelatinization.

A representative number of kernels for a grain or variety to be tested may about 10, about 15, about 20, about 40, or more.

Similar amounts of starch should be exposed within a kernel type or strain to maintain consistent results.

Any container may be used that is sufficiently large to hold the kernel and the reagents. Examples include microfuge tube racks, microtiter plates, test tubes, microfuge tubes, centrifuge tubes, and 96-well plates. It is within the ability of one skilled in the art to adjust the reagents used in the various reactions based on the container.

Starch Gelatinization

After preparing the kernel to expose the starch, the amylose portion of the starch is then gelatinized in order to make it more accessible to molecules which can qualify the amount of amylose within the kernel. Gelatinization of amylose generally consists of three phases: 1) the solvent is absorbed into the amorphous spaces within the starch leading to the swelling of the starch; 2) the solvent then enters into the more tightly bound areas, such as areas of amylopectin double helices, causing the starch to become more diffuse and causing the amylose chains to being to dissolve resulting in the breaking down of the crystalline regions into more amorphous forms; and 3) the solvent penetrates into these amorphous regions, causing more swelling and the disintegration of the crystalline structures as the amylose molecules are dissolved into the solvent. Heat may be applied to help the swelling process by providing additional energy for the solvent to interact with amylose hydroxyl units depending on the solvent, the kernel type, the amount of water, pH, damage to the starch, and the concentrations of salts, fats, and proteins. The amylose will aggregate into a gel at room temperature or if heat is applied, during the cool down phase.

To gelatinization the amylose, the kernel is submerged in a solvent to disperse or dissolve the exposed amylose within the starch. The solvent may interact with the hydroxyl groups on the amylose to relax the crystalline structure of the starch to cause swelling while maintaining the linear coil for downstream interaction with a detection molecule.

The amylose may be dissolved or dispersed by exposing the prepared kernel to a sufficient amount of a solvent, for example dimethyl sulfoxide (DMSO), a halogen salt, a strong base, or a strong acid. As used here a "sufficient amount of solvent" means enough to completely submerge the kernel during the entire gelatinization process and to account for any loss during evaporation if electromagnetic radiation is applied. The solvent may be sufficient to gelatinize the amylose or additional energy may be needed in addition to the solvent to gelatinize the amylose.

In an embodiment, DMSO may be used as a solvent. The concentration of the DMSO may be from about 90% v/v to about 100% v/v. In a more preferred embodiment, DMSO is combined with urea (UDMSO) where urea is from about 300 mM to about 1,000 mM, from about 400 mM to about 800 mM, or from about 500 mM to about 700 mM in the UDMSO solvent. In another embodiment, iodine may be added to the DMSO ($I_2$DMSO).

In other embodiments, a halogen salt may be used as a solvent. For example, calcium fluoride, calcium bromide, calcium chloride, calcium iodine beryllium chloride, magnesium chloride, strontium chloride, barium chloride, or radium chloride may be used. In a preferred embodiment the solvent is calcium chloride. The concentration of the halogen salt solvent may be from about 0.5 M to about 6 M, from about 1 M to about 5 M, or from about 2 M to about 4 M.

In yet other embodiments, the solvent may be a strong base. Strong bases include Arrhenius and Lewis basis. Examples of strong bases include potassium hydroxide, sodium hydroxide, barium hydroxide, cesium hydroxide, strontium hydroxide, calcium hydroxide, lithium hydroxide, rubidium hydroxide, butyl lithium, lithium diisopropylamide, lithium diethylamide, sodium amide, sodium hydride, and lithium bis(trimethylsilyl)amide. In some embodiments where the detection molecule is unstable in alkaline solutions, for example iodine species, the base may then at least partially neutralized with an organic acid after the amylose has gelled. Examples of suitable organic acids include lactic acid, acetic acid, glycolic acid, propionic acid, 3-hydroxypropanoic acid, malonic acid, butyric acid, or hydroxybutyric acid. The concentration of the base may be from about 0.1 M to about 8 M, from about 0.5 M to about 7 M, or from about 1 to about 5 M.

In yet other embodiments, a strong acid may be used as the solvent. Exemplary preferred strong acids include hydrochloric acid, nitric acid, sulfuric acid, hydrobromic acid, perchloric acid, or chloric acid. The concentration of the acid may be from 0.1 M to 12 M, from about 1 to about 5 M, or from about 2 to about 4 M.

In some embodiments, the kernel in the solvent may be exposed to electromagnetic radiation to quickly add the additional energy to the interaction between the solvent and the amylose for a sufficient amount of time to allow the solvent to penetrate into the amylose. This penetration may cause the amylose to swell or may cause the disintegration of the crystalline structure. In a preferred embodiment the electromagnetic radiation is microwave. The kernel in the solvent may be exposed from about 1 to about 90 seconds, from about 10 to about 75 seconds or from about 10 to about 60 seconds. Preferably, the kernel in the solvent is exposed for about 60 seconds or less.

After exposure to electromagnetic radiation, in some embodiments the kernel in the solvent is allowed to cool for about 10 minutes or less, for about 5 minutes or less, or for about 2.5 minutes or less. The cooldown time should be kept constant for each grain or variety to maintain consistent results. During the cooling period the amylose will aggregate into a gel.

In other embodiments the kernel is incubated within the solvent without applying electromagnetic radiation for a sufficient amount of time. The incubation time should be kept constant for each grain or variety to maintain consistent results. The incubation time may be from about 0.5 minute to about 15 minutes, from about 2.5 minutes to 10 minutes, or from about 2.5 to about 7.5 minutes. It is preferable to neutralize strong bases either after heating or after the incubation with the base if the detection molecule is unstable in alkaline conditions.

While enzymes may be used to break apart the crystalline structures, they are not preferred due to the time needed for the reaction to occur and the possible loss of the linear chain as enzymes such as α-amylase, and amyloglucosidase, convert amylose into simple sugars and may reduce the signal.

The amount of solvent, the concentration of the compounds, and the heating or incubation length may be determined by any method known in the art for a particular grain or strain. In a preferred embodiment, various serial dilutions of the concentration of the solvent with kernels of various sizes and different heating or incubation methods may be used to determine the optimal combination of factors.

Visualization

Gelatinization of the amylose makes the liner coils more accessible to molecules that will interact with the interior of the coil and enzymes. These molecules are hydrophobic and include iodine, fatty acids, or aromatic compounds.

While any method of detecting and determining the amylose content known in the art may be used, in a preferred embodiment, the detection molecule is iodine. As used herein, a "detection molecule" refers to any molecule that will interact with the amylose chain to allow a qualitative differentiation between high amylose kernels and normal or low amylose kernels.

Iodine interacts with the gelatinized amylose to cause a rapid color change of the solution to a blue or blue-black color. Iodine interacts with amylopectin to turn a reddish-yellow or brown color. As shown in more details in the examples, potassium iodide iodine ($KI_2$) is the preferred compound for rapid amylose visualization due to rapid coloration and solubility with water and the solvent. Similar to other compounds, $KI_2$ concentrations may need optimization for specific grains or varieties given the amount of amylose in the start and how much of the starch is exposed for gelatinization.

Verification

Figure 1B:
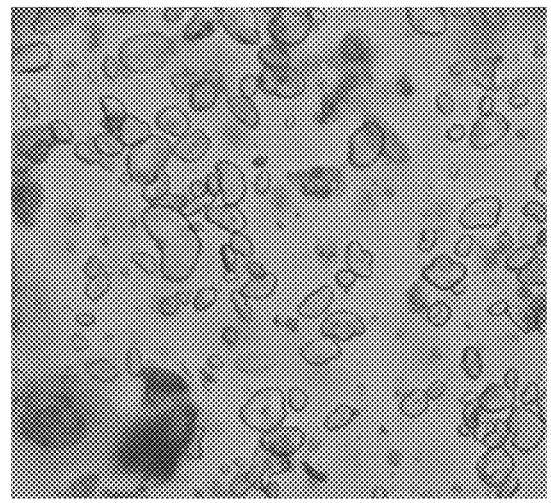
FIG. 1B shows exemplary high amylose wheat under microscopy having an irregular shape.
Figure 1C:
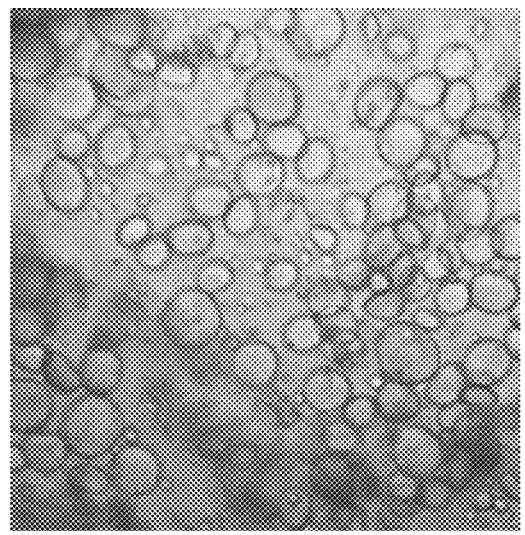
FIG. 1C shows exemplary control wheat under microscopy having a round shape.

If the color becomes light blue or light purple, verification of the amylose content may be preformed using a microscope. In a preferred embodiment, the kernel may be crushed in water and then a drop may be placed onto a slide with a cover slip. Viewing under the microscope will confirm if the kernel is a high amylose (FIG. 1B) or normal or low amylose (FIG. 1C).

Optionally, if iodine is the detection molecule, a spectrophotometer may be used to read the absorbance for amylase and/or amylopectin. Amylose may be read at about 620 nm to about 630 nm and amylopectin may be read at about 460 nm to about 550 nm. Absorbency thresholds may be calculated, for example, by averaging the high amylose samples and the normal or low amylose samples within a plate or be based off results from previous microscopy verifications.

If iodine is the detection molecule, the differences in amylopectin may also be assessed as the iodine turns a different and distinct color from that of amylose.

Exemplary Rapid Amylose Procedure for the Lab

If the Rapid Amylose Procedure (RAP) is to be performed in the lab with access to typical lab equipment, for example a microwave and microfuge racks, a preferred embodiment of RAP for wheat is as follows.

Reagent Prep
1. Deionized water or distilled water
2. Urea 6 M Dissolve 36 g of urea (Sigma ref U5378) in deionized water. Adjust the volume to 100 ml. Stable for 3 months at 4° C.
3. UDMSO Add 9 volumes of DMSO (dimethyl sulfoxide) (Sigma ref 34869) to 1 volume of urea 6 M
4. $KI_2$ solution Dissolve 0.5 g of iodine, ID, Merck ref 1.04761.0100) and 5 g of potassium iodine, KI (Merck 1.05043.0500) in 250 ml Deionized water. Stable for 6 months at room temperature in dark bottle storage (foil covered bottle or amber glass bottle).

Equipment
1. While any pipette will work, a repeating pipette is preferred due to the speed advantage, and 1, 5, and 25 ml pipette tips.
2. Seed cutter for ease of splitting the kernel in half
3. Heat source, preferably a microwave for speed
4. A microwave safe rack and/or vial (glass or plastic), for example a clear 2 ml microfuge rack Rapid Amylose Procedure (RAP)
1. Obtain representative samples of kernels. Cut the seeds in half using the seed cutter.
2. Obtain a 2 ml centrifuge rack and put a germ half into each well.
   a. If both halves will be used, this will be count as one kernel. It is best preferred to use only one side of the wheat kernel.
   b. It is preferred to use the kernels that are cut in approximately half and to maintain a similar size between kernels.
3. It is preferred to include up to 3 wells of control normal wheat, and up to 3 wells of HAW wheat kernel control (FIG. 1A).
4. To gelatinize, use the repeating pipette, add sufficient UDMSO (one-part UDMSO is 200 μl) to cover the kernel
5. Shake the whole rack for 5 seconds to make sure the UDMSO covers the seed.
6. Microwave the whole rack on high for 1 min.
7. Shake for 5 sec.
8. Cool on the bench for 5 min. Keep the wait time consistent.
9. Add 20 μl of $KI_2$ into each well.
10. Add 1500 μl of deionized or distilled water into each well.
11. The color should develop immediately.
    HAW seeds are dark purple/blue color
    normal wheat is clear/yellow
12. Add additional 60 ul of $KI_2$ into all the wells and shake.
13. Immediately count the number of wells containing normal wheat (clear, yellow).
14. If the color turns out to be in between (light purple), confirm the sample using microscope.
    a. Take the seed from the well and put it in a pestle and mortar.
    b. Add approx. 250 ul of water.
    c. Grind the sample
    d. Drop sample onto the microscope slide and put the cover slide on.
    e. Look under microscope and confirm.
15. Report Number of contaminants per total number of seed (example: 3/50)

As shown by the above exemplary method, the traditional requirements of extracting the starch, drying overnight, then using a spectrophotometer against a known standard curve are not needed. This allows for a rapid, less than 10-minute test for high amylose kernels.

Exemplary Rapid Amylose Procedure for the Field

As not every solvent needs electromagnetic radiation to gelatinize the starch and given the speed and ease of use of the RAP, it may be used in a field situation where access to certain lab equipment, like a microwave, is limited. Further, as acid and base solutions are stable in the long term at room temperature, no refrigeration is needed for certain embodiments. A preferred example using minimal equipment of RAP for wheat which may be used in the field or remote locations is as follows:

Reagent Prep
1. Deionized water or distilled water
2. 2 M KOH
3. 85% lactic acid
4. $KI_2$ solution Dissolve 0.5 g of iodine, ID, Merck ref 1.04761.0100) and 5 g of potassium iodine, KI (Merck 1.05043.0500) in 250 ml Deionized water. Stable for 6 months at room temperature in dark bottle storage (foil covered bottle or amber glass bottle).

Equipment
1. While any pipette will work, a repeating pipette is preferred due to the speed advantage, and 1, 5, and 25 ml pipette tips.
2. Seed cutter for ease of splitting the kernel in half
3. Any vial may be used, preferably centrifuge or microfuge tubes with at least a 2 mL volume or a clear rack may be used.

Rapid Amylose Procedure (RAP)
1. Obtain representative samples of kernels. Cut the seeds in half using the seed cutter.
2. Put a germ half into each well.
   a. If both halves will be used, this will be count as one kernel. It is best preferred to use only one side of the wheat kernel.
   b. It is preferred to use the kernels that are cut in approximately half and to maintain a similar size between kernels.
3. It is preferred to include 3 wells of control normal wheat, and 3 wells of HAW wheat kernel control (FIG. 1A).
4. To gelatinize, use the repeating pipette, add 200 µl 2 M KOH (one part) to cover the kernel—Shake the whole rack for 5 seconds to make sure the KOH covers the seed.
5. Allow for about a 5 minute incubation
6. Shake for 5 sec.
7. Add 100 µL 85% lactic acid (one-half part)
8. Allow for about a 5 minute incubation
9. Add 20 µl of $KI_2$ into each well.
10. Add 1500 µl of deionized or distilled water into each well.
11. The color should develop immediately.
    HAW seeds are dark purple/blue color
    normal wheat is clear/yellow
12. Add additional 60 ul of $KI_2$ into all the wells and shake.
13. Immediately count the number of wells containing normal wheat (clear, yellow).
14. If the color turns out to be in between (light purple), confirm the sample using microscope.
    a. Take the seed from the well and put it in a pestle and mortar.
    b. Add approx. 250 ul of water.
    c. Grind the sample
    d. Drop sample onto the microscope slide and put the cover slide on.
    e. Look under microscope and confirm.
15. Report Number of contaminants per total number of seed (example: 3/50)

The invention is further described in detail by reference to the following experimental examples. These examples are provided for purposes of illustration only and are not intended to be limiting unless otherwise specified. Thus, the invention should in no way be construed as being limited to the following examples, but rather, should be construed to encompass any and all variations which become evident as a result of the teaching provided herein.

EXAMPLES

Example 1

Exemplary Rapid High Amylose Wheat (HAW) seed purity test (Rapid Amylose Procedure (RAP))

The is an exemplary test for a rapid and qualitative method use to differentiate high amylose and non-high amylose wheat. Total test time: Less than 10 min
Equipment
1. Repeating pipette and 1, 5, and 25 ml pipette tips.
2. Seed cutter
3. Microwave
4. Clear 2 ml centrifuge rack Reagents
1. Deionized water or distilled water
2. Urea 6 M Dissolve 36 g of urea (Sigma ref U5378) in deionized water. Adjust the volume to 100 ml. Stable for 3 months at 4° C.
3. UDMSO Add 9 volumes of DMSO (dimethyl sulfoxide) (Sigma ref 34869) to 1 volume of urea 6 M
4. I2-KI solution Dissolve 0.5 g of iodine, ID, Merck ref 1.04761.0100) and 5 g of potassium iodine, KI (Merck 1.05043.0500) in 250 ml Deionized water. Stable for 6 months at room temperature in dark bottle storage (foil covered bottle or amber glass bottle).

Rapid Amylose Procedure (RAP)
1. Obtain representative samples of seeds. Cut the seeds in half using the seed cutter.
2. Obtain a 2 ml centrifuge rack and put a germ half into each well.
3. Include 3 wells of control normal wheat, and 3 wells of HAW wheat seed control.
4. Using repeating pipette, add 100111 UDMSO (one-half part)—Shake the whole rack for 5 secs to make sure the UDMSO covers the seed (we want to gelatinize the starch with UDMSO).
5. Microwave the whole rack on high for 1 min.
6. Shake for 5 sec.
7. Cool on the bench for 5 min. Keep the wait time consistent.
8. Add 20111 of 12-KI into each well.
9. Add 1500 µl of deionized or distilled water into each well.
10. The color should develop immediately.
    HAW seeds are purple/blue color
    Normal wheat is clear/yellow
11. Add additional 60 ul of $KI_2$ into all the wells and shake.
12. Immediately count the number of wells containing normal wheat (clear, yellow).
13. If the color turns out to be in between (light purple), confirm the sample using microscope.
    a. Take the seed from the well and put it in a pestle and mortar.
    b. Add approx. 250 ul of water.
    c. Grind the sample
    d. Drop sample onto the microscope slide and put the cover slide on.
    e. Look under microscope and confirm.
14. Report Number of contaminants per total number of seed (example: 3/50)

Exemplary Calculation:

| | Total number of half seeds | Count of normal wheat | Contamination % (Normal Seed/Total seeds) | Purity % |
|---|---|---|---|---|
| Example | 50 | 3 | 6% | 94% |

Example 2

Control Experiment for RAP (Rapid Amylose Procedure) Expansion

Use QN0000524, a Healthsense 253 high amylose variety, to set up baseline purity values and to offer a comparison to subsequent tests.
Samples: QN0000524 HS253. This was done using three trays of 80 half-kernels each.
Reagents: UDMSO (Urea-Dimethyl Sulfoxide), Distilled Water, $KI_2$ (Potassium Iodide Iodine)

Results:

|        |       |             |
|--------|-------|-------------|
| Tray 1 | 10/80 | 87.5% Pure  |
| Tray 2 | 9/80  | 88.75% Pure |
| Tray 3 | 6/80  | 92.5% Pure  |

These results show that the average purity of the HAW, variety QN000524 HS253, is about 89.58% using standard RAP.

Example 3

Urea Free DMSO

Ran Standard RAP method, as in Example 1, on samples QN0000524, a High Amylose control, and a generic winter wheat, low amylose control, with only one change to the procedure: UDMSO will be replaced with equal parts DMSO (no urea).
Sample: QN0000524 HS253 Variety, generic winter wheat. This was done on three trays, with each tray having 40 half kernels each.
Reagents: $KI_2$, Distilled Water, Dimethyl Sulfoxide ~99.7%
Results

| QN0000524 |      |            |
|-----------|------|------------|
| Tray 1    | 4/40 | 90% Pure   |
| Tray 2    | 1/40 | 97.5% Pure |
| Tray 3    | 5/40 | 87.5% Pure |

| Generic Winter Wheat |       |         |
|----------------------|-------|---------|
| Tray 1               | 40/40 | 0% Pure |
| Tray 2               | 40/40 | 0% pure |
| Tray 3               | 40/40 | 0% Pure |

Figure 2A:
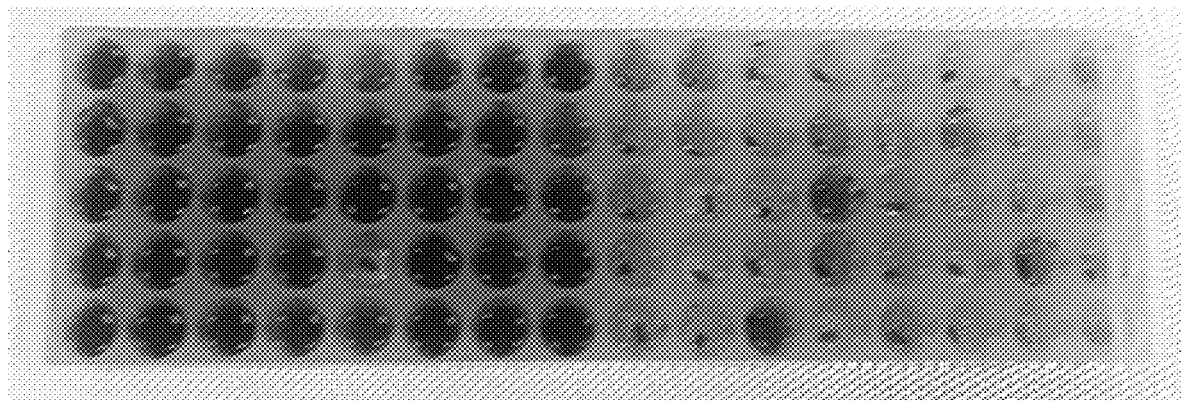
FIG. 2A shows an exemplary tray comparing high amylose wheat to control wheat when urea is not added to the DMSO in the gelatinization step of RAP.
Figure 2B:
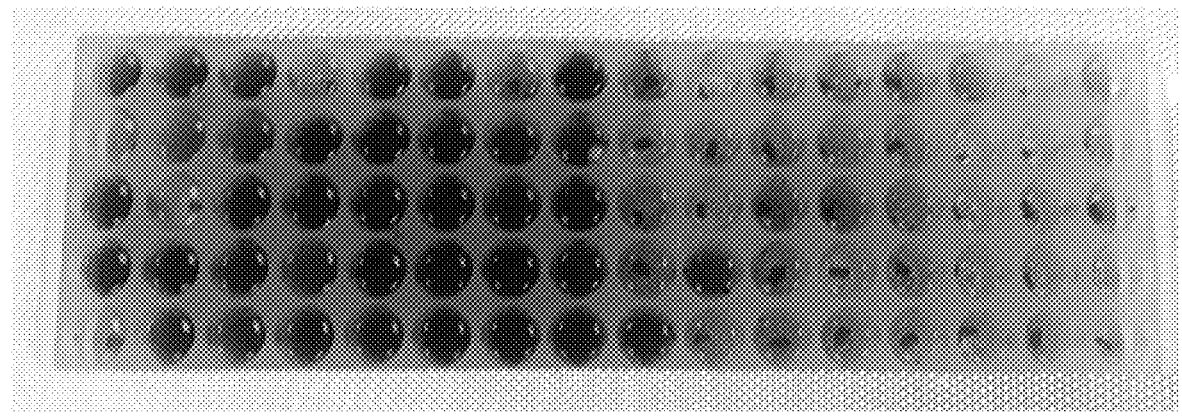
FIG. 2B shows an exemplary tray comparing high amylose wheat to control wheat when urea is not added to the DMSO in the gelatinization step of RAP.

Tray 2 (FIG. 2A) and Tray 3 (FIG. 2B) showed false positives in the generic winter wheat samples. Generic winter wheat on Tray 2 had 2 dark false positives and Tray 3 had 2 false positives as well. These would have been considered High Amylose if they had been run in a normal batch. A False positive is a non-high amylose samples that reacts with the chemicals to produce the dark blue color of high amylose samples. While samples may show a false positive, confirmation under the microscope, as described in Example 1, can be performed to verify their amylose level.

As similar results were obtained for the HAW as in Example 2, the inclusion of the urea in the DMSO is an optional ingredient.

Example 4

6 M Urea Only

This test ran the Standard RAP method but substitute UDMSO for equal parts Urea 6 M. Urea was brought to room temperature one hour prior to use.
Samples: QN0000524 HS253, Generic Winter wheat. This was done on two trays, with each tray having 40 half kernels each.
Reagents: Potassium Iodide Iodine, Urea 6 M, Distilled Water.

Results:

| QN0000524 |      |            |
|-----------|------|------------|
| Tray 1    | 3/40 | 92.5% Pure |
| Tray 2    | 4/40 | 90% Pure   |

| Generic Winter Wheat |       |         |
|----------------------|-------|---------|
| Tray 1               | 40/40 | 0% Pure |
| Tray 2               | 40/40 | 0% Pure |

Figure 3:
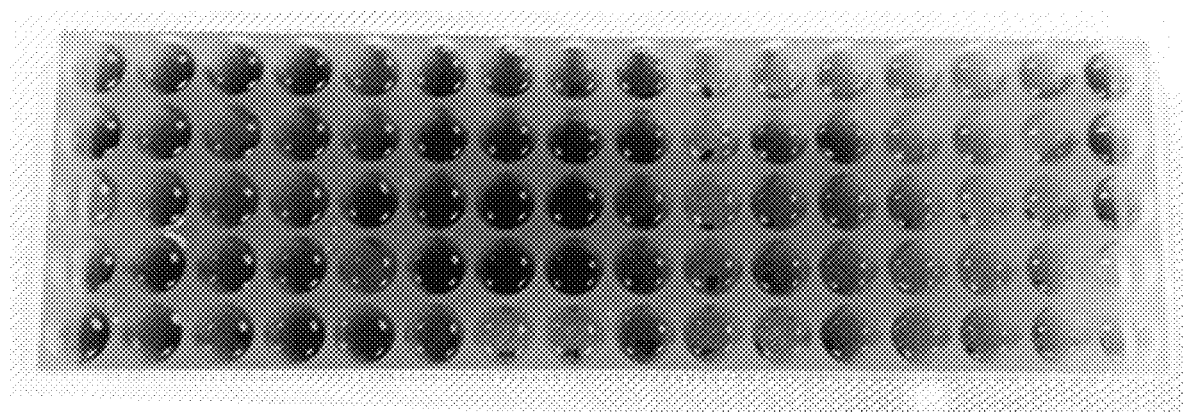
FIG. 3 shows an exemplary tray comparing high amylose wheat to control wheat when 6 M urea is used in place of UDMSO during the gelatinization step of RAP.

As shown in FIG. 3, the samples gave off a green tone instead of the blue and yellows as seen in Example 2 and 3, above. This made the results indistinguishable for most samples without microscopy. Due to this, the 6 M urea alone is not sufficient to be used as rapid qualitative test for wheat.

Example 5

3 M Urea Only

Figure 4:
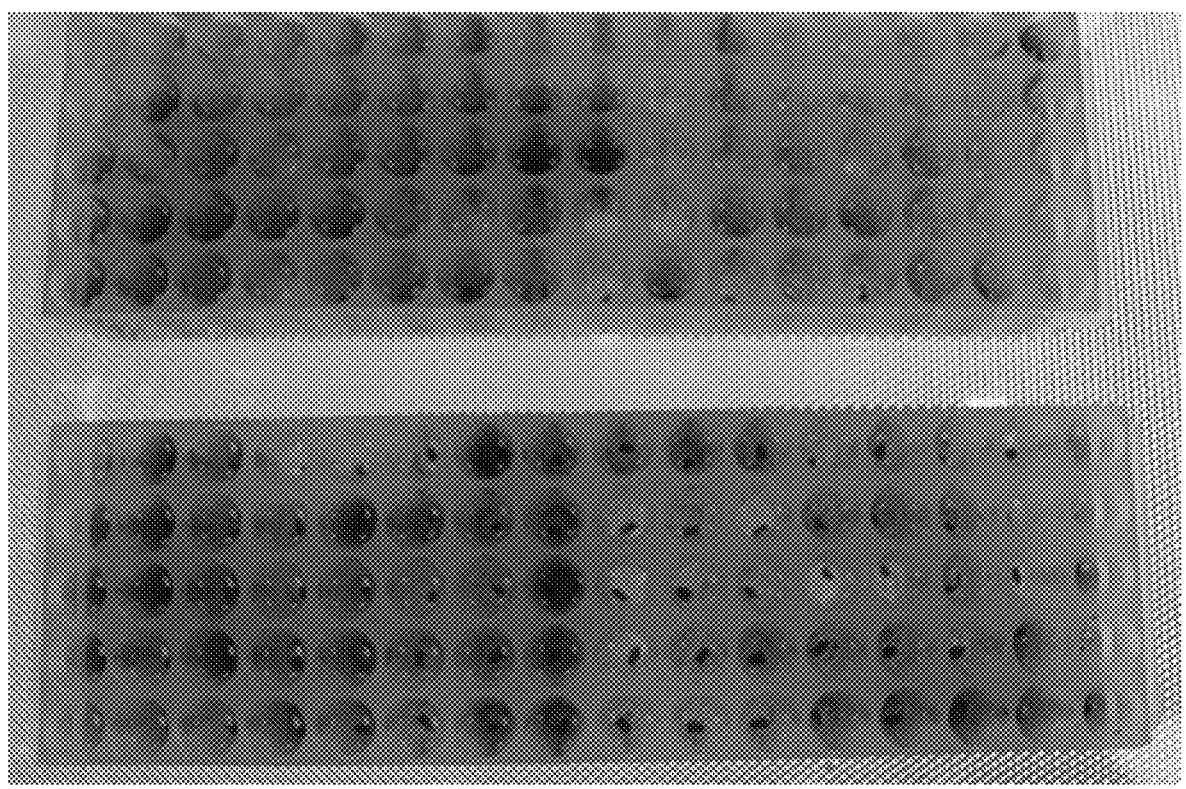
FIG. 4 shows two exemplary trays comparing high amylose wheat to control wheat when 3 M urea is used in place of UDMSO during the gelatinization step of RAP.

This test ran the Standard RAP method but substitute UDMSO for equal parts Urea 3 M. Urea was brought to room temperature one hour prior to use.
Samples: QN0000524 HS253, Generic Winter wheat. This was done on two trays, with each tray having 40 half kernels each.
Reagents: Potassium Iodide Iodine, Urea 6 M, Distilled Water.
Results: Inconclusive As in Example 4, above, no clear color was produced to differentiate the samples. HAW appears with the same coloration as the winter wheat and has the same green tint. Both test trays (FIG. 4) failed in this same way. Therefore, like Example 4, 3 M urea is unable to produce clear enough results to be used as a rapid qualitative test for wheat.

Example 6

Water Only

In this experiment, we will run the standard RAP method but replace UDMSO with equal parts distilled water.
Samples: QN0000524 HS253, Generic Winter Wheat. This was done on two trays, with each tray having 40 half kernels each.
Reagents: Distilled Water, $KI_2$.
Results: Inconclusive.

Figure 5A:
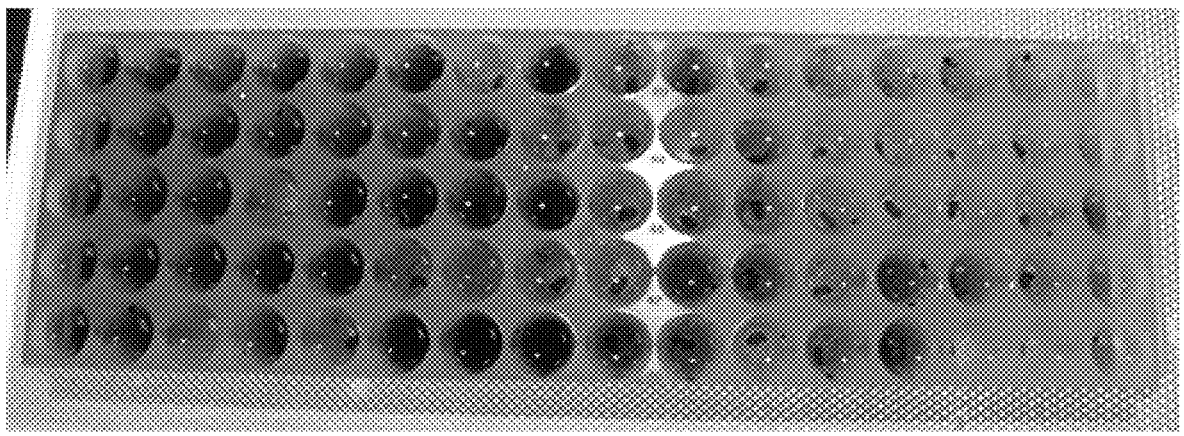
FIG. 5A shows an exemplary control tray of RAP comparing high amylose wheat to control wheat.
Figure 5B:
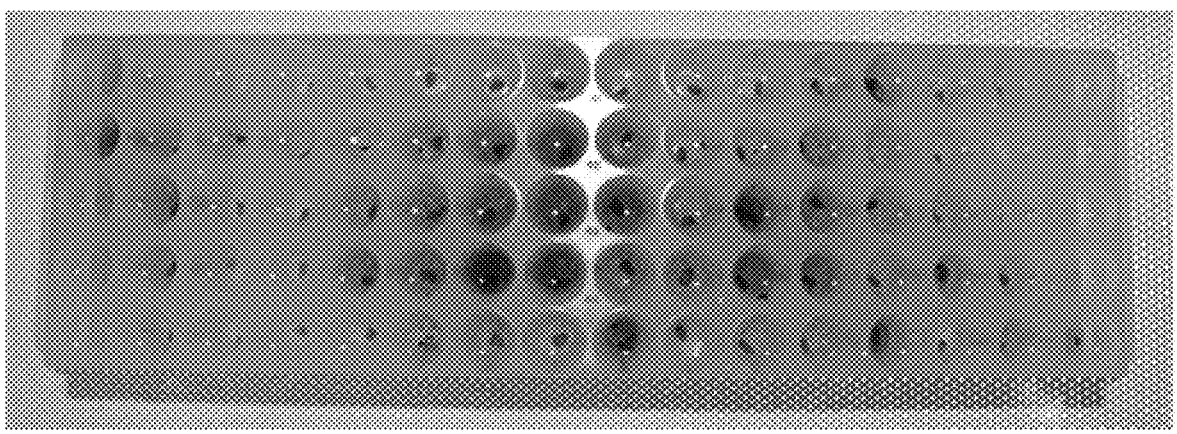
FIG. 5B shows an exemplary try of replacing the UDMSO with equal part distilled water.
Figure 5C:
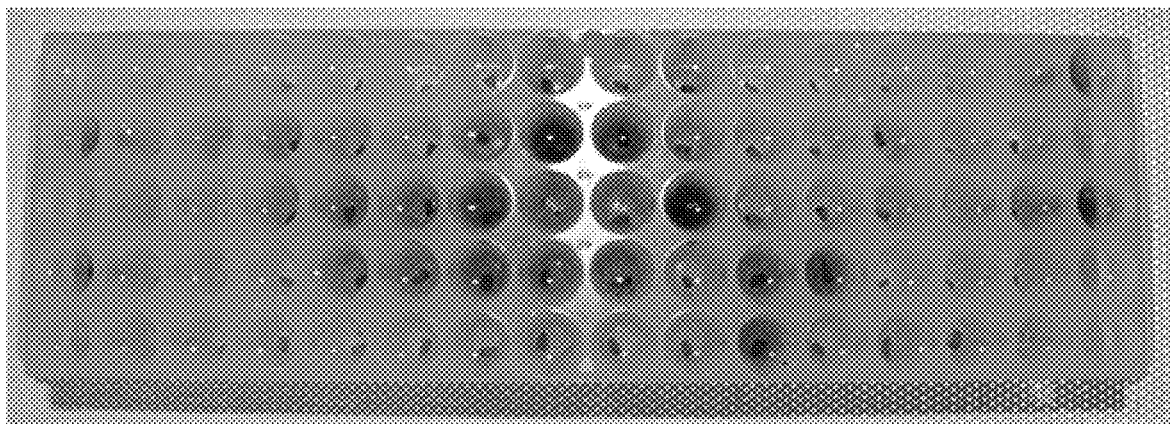
FIG. 5C shows an exemplary try of replacing the UDMSO with equal part distilled water.

In contrast to a control tray (FIG. 5A), both test trays (FIGS. 5B-C) produced inconclusive results. for most of the seeds, no coloration from the off-yellow color of low amylose occurred. Very few changed from the addition of Potassium Iodide Iodine, and no consistent pattern could be discerned from the few that did. This method does not work for a rapid test as the start is solubilized rapidly enough.

Example 7

UDMOS Substituted with $I_2DMSO$

In this experiment a first set of samples were prepared using the standard RAP test but replace UDMSO with equal parts Iodine-Dimethyl Sulfoxide ($I_2DMSO$). After microwaving, distilled water was added since Iodine is present in the $I_2DMSO$.

A second set of samples was prepared and ran with the following adjustment to the first set:

The RAP test will be performed as normal with I$_2$DMSO replacing UDMSO in equal parts. KI$_2$ was added after microwaving per normal, instead of excluding it.

A third set of samples was prepared and run with the following adjustment: The RAP test as normal with UDMSO replaced with double its amount of I$_2$DMSO. No KI$_2$ will be added after microwaving.

Samples: QN0000524 HS253, Generic winter wheat.

Reagents: Iodine-Dimethyl Sulfoxide (I$_2$DMSO), Distilled Water. This was done on one tray, with having 40 half kernels each.

Results: Inconclusive.

Figure 6A:
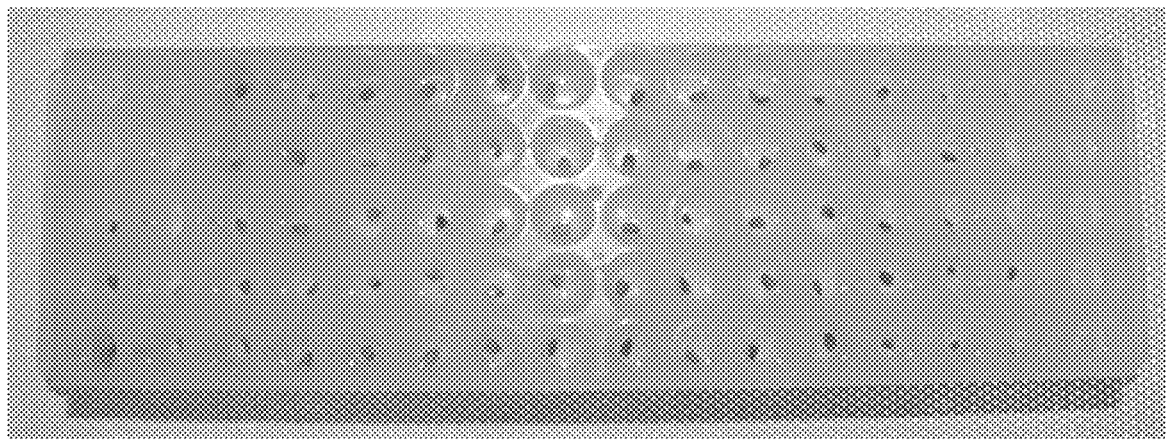
FIG. 6A shows an exemplary tray of RAP where $I_2DMSO$ is used in equal parts and replaced UDMSO and no additional $KI_2$ is added after heating.
Figure 6B:
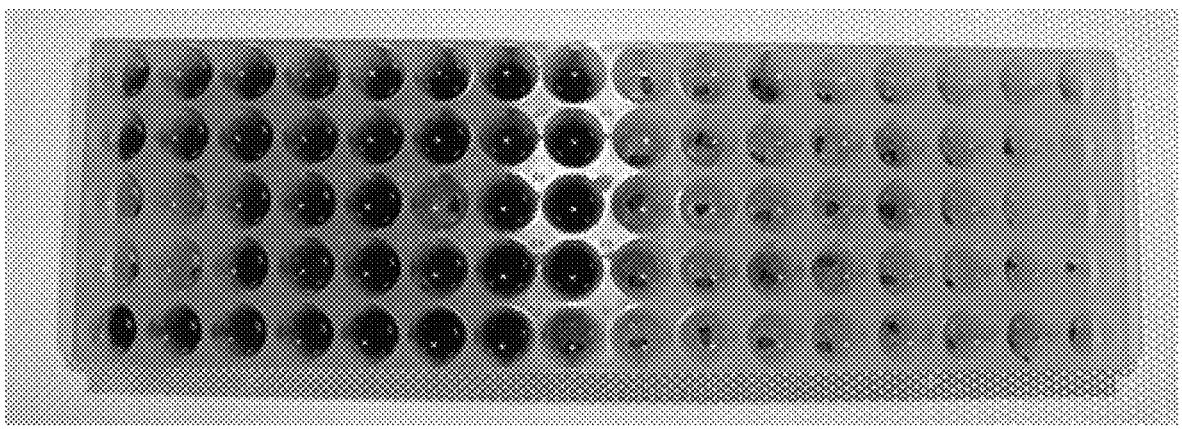
FIG. 6B shows an exemplary tray of RAP where $I_2DMSO$ is used in equal parts and replaced UDMSO with normal $KI_2$ added after heating.
Figure 6C:
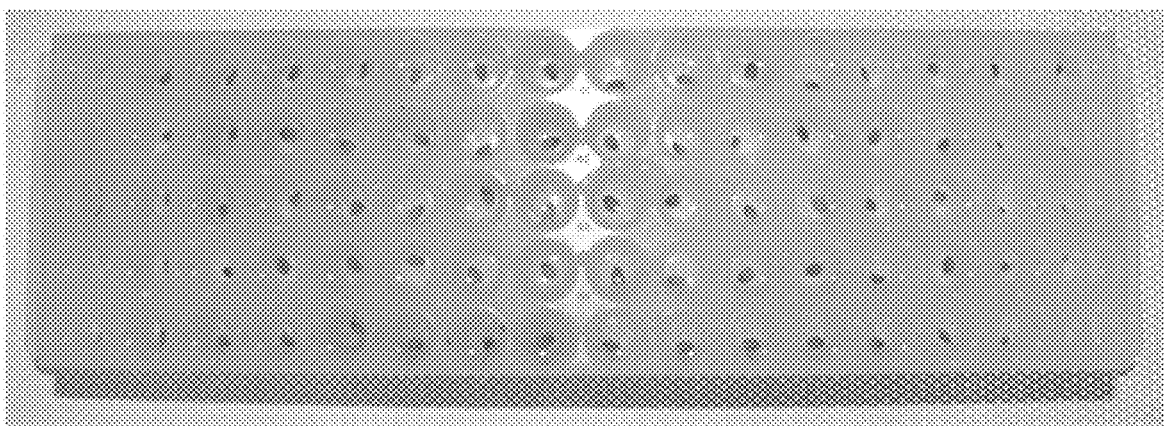
FIG. 6C shows exemplary tray of RAP where $I_2DMSO$ was doubled and replaced UDMSO and no additional $KI_2$ is added after heating.

I$_2$DMSO alone at either concentration did not create any color in the samples other than a slight pink hue in a few of the samples (FIG. 6A for first set; FIG. 6C for the third set). Additional addition of KI$_2$ (Potassium Iodide Iodine) after performing RAP on the second set produced coloration (FIG. 6B). The doubling of I$_2$DMSO, first set versus third set, resulted in more samples turning slightly pink. I$_2$DMSO can replace UDMSO, but the addition of KI$_2$ after microwave cooldown is needed or insufficient coloration will occur.

| Second set: | |
|---|---|
| QN0000524 HS253 | Generic Winter Control |
| 5/40 | 40/40 |
| 87.5% Pure | 0% Pure |

Example 8

In this experiment, a first set of samples will run the RAP test replacing UDMSO with equal parts 3 M CaCl$_2$ (calcium chloride). A second set of samples with double the amount of CaCl$_2$ of the UDMSO to mitigate evaporation loss. A third set of samples will be run without microwaving with an equal amount of CaCl$_2$ to the UDMSO.

Samples: QN0000524 HS253, Generic Winter Wheat. Each set was done on one tray, with having 40 half kernels each.

Reagents: Calcium Chloride 3 M, Potassium Iodide Iodine, Distilled Water.

Results:

| First set: | |
|---|---|
| QN0000524 HS253 | Generic Winter Wheat |
| 5/40 | 40/40 |
| 87.5% Pure | 0% Pure |

| Second set: | |
|---|---|
| QN0000524 HS253 | Generic Winter Wheat |
| 2/40 | 40/40 |
| 95% Pure | 0% Pure |

Figure 7A:
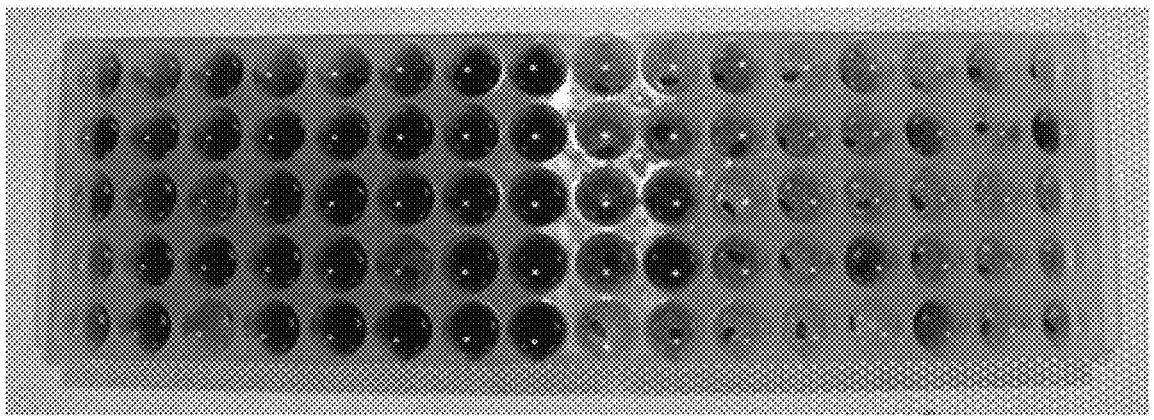
FIG. 7A shows an exemplary tray of RAP where 3 M $CaCl_2$ was used in equal parts to and in place of UDMSO.
Figure 7B:
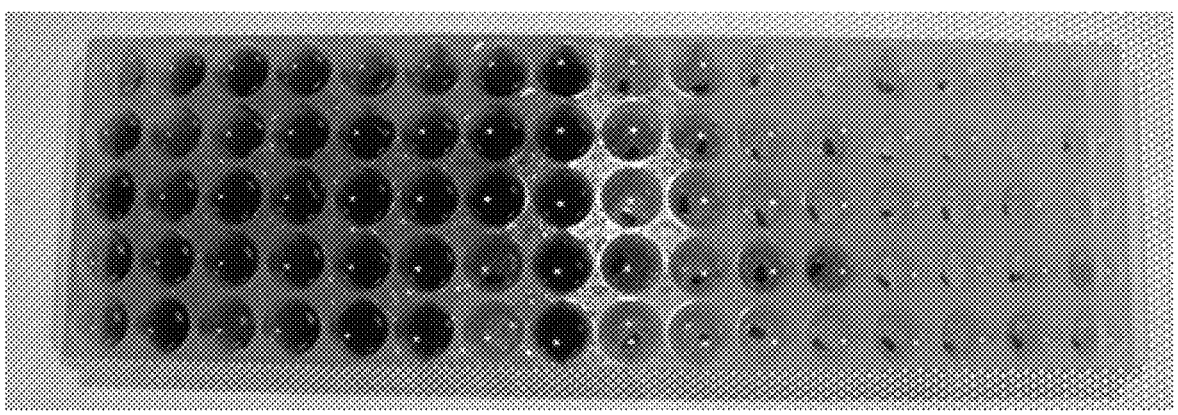
FIG. 7B shows an exemplary tray of RAP where 3 M $CaCl_2$ was used in double parts to and in place of UDMSO.
Figure 7C:
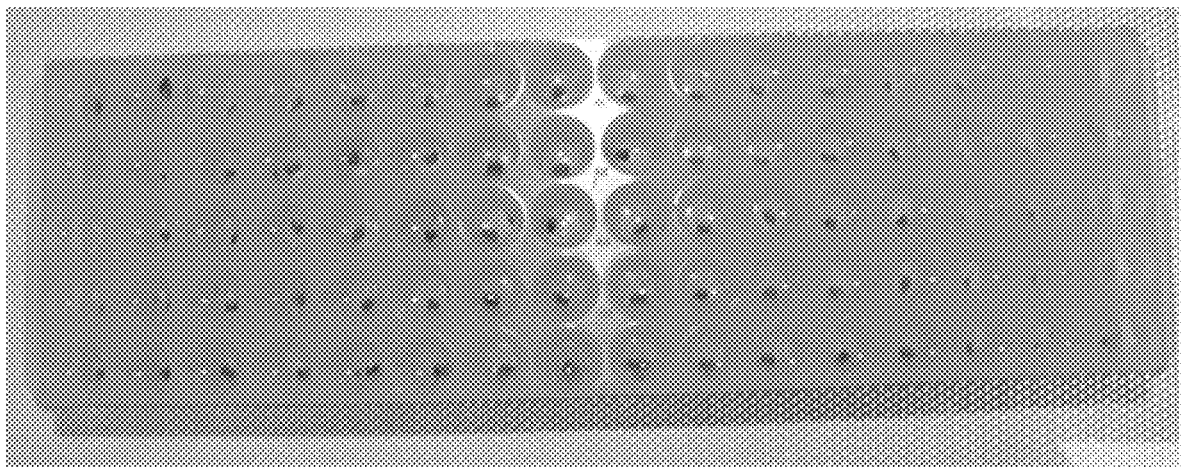
FIG. 7C shows an exemplary tray of RAP where 3 M $CaCl_2$ was used in equal parts to and in place of UDMSO and without microwaving.

In the first set, calcium chloride appeared to have gelatinized on the sides of the sample hole on the tray. Much of the calcium chloride evaporated as well. Lots of samples appeared as in-between or intermediate (to faint a blue color to tell if high or low amylose without microscopy) or as false positives (FIG. 7A). The second set performed adequately. Doubling the calcium chloride to mitigate loss during heating works for a rapid test using a microwave (FIG. 7B). The third set indicated all samples were low amylose (FIG. 7C). Therefore, using sufficient CaCl$_2$ to prevent loss during heating may be used as a rapid test.

Example 9

Use of NaOH in Place of UDMSO

To further determine what solvents may be used to sufficiently dissolve or gelatinize the amylose from the seeds, UDMSO was replaced with a strong base, specifically NaOH and/or an acid. Unless otherwise stated, all other parameters were the standard RAP procedure.

A first set was replaced UDMSO with equal parts 1 M NaOH and follow standard RAP.

A second set doubled the volume of NaOH as the first set due to evaporation seen in the first set.

A third set uses the same volume of NaOH as the second set but increases the concentration to 4M.

A fourth set extends the rest time to 10 minutes from the standard five used in the third set.

A fifth set replaces the UDMSO with an equal part of 4M NaOH and an extra volume of distilled water prior to heating in a microwave.

A sixth set replicated the fifth set, but without microwaving.

A seventh set replaced the UDMSO with an equal part 4 M NaOH and following microwaving, a one-half part 85% lactic acid was added to form sodium lactate and water prior to the addition of the KI$_2$ and distilled water.

An eighth set replicated the seventh set but with double the NaOH.

A ninth set replaced the UDMSO with a one-half part 4 M NaOH and one-half part 85% lactic acid prior to heating.

A 10$^{th}$ set replicated the ninth set but will not heat with a microwave, instead allowing for a five-minute incubation between the addition of NaOH and lactic acid and another five-minute incubation after the addition of lactic acid.

An 11$^{th}$ set replaced the UDMSO with an equal amount of 85% lactic acid and a one-half amount of 4 M NaOH and follow the 10$^{th}$ set procedure.

A 12$^{th}$ set followed the same procedure as the 10$^{th}$ set but with double the NaOH.

A 13$^{th}$ set followed the same procedure as the 10$^{th}$ set but with three times (1.5-parts) the NaOH.

A 14$^{th}$ set will follow the same procedure as the 10$^{th}$ set but with three times the NaOH and twice the lactic acid.

Sample: QN0000524 HS253, Generic Winter Wheat. Each set was done in 1 tray with 40 half kernels of each variety.

Reagents: Sodium Hydroxide 1 M or 4 M, Potassium Iodide Iodine, Distilled Water, 85% Lactic Acid.

Figure 8A:
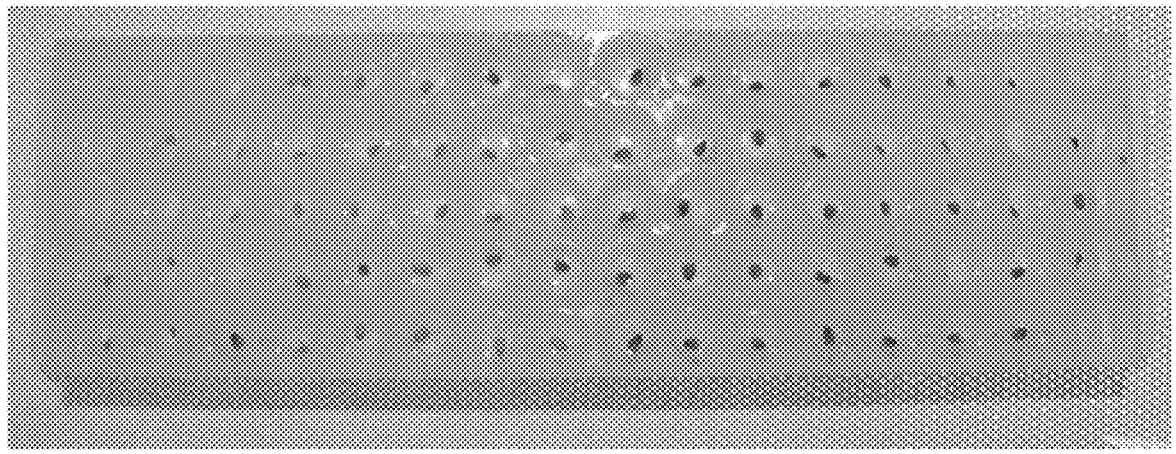
FIG. 8A shows an exemplary tray of RAP where UDMSO was replaced with equal parts 1 M NaOH.
Figure 8B:
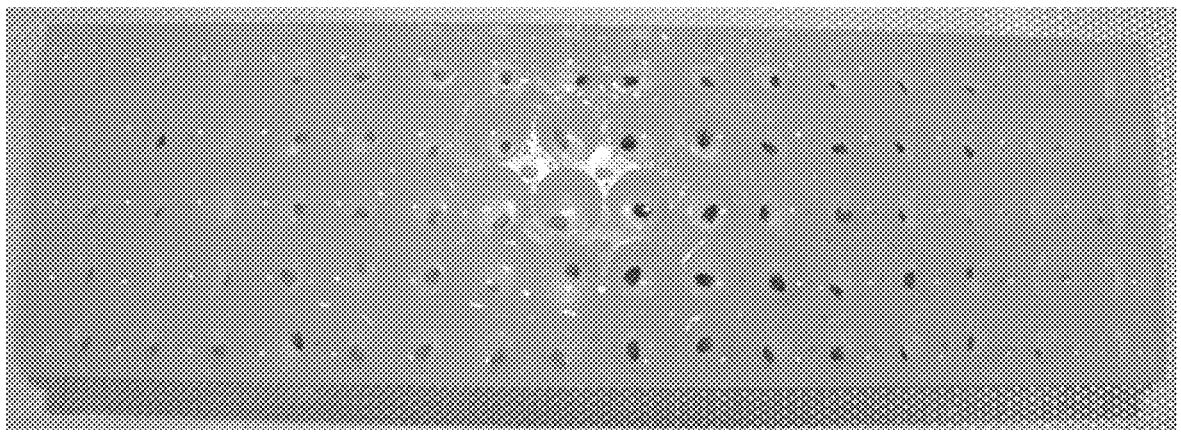
FIG. 8B shows an exemplary tray of RAP where UDMSO was replaced with two-parts 1 M NaOH.
Figure 8C:
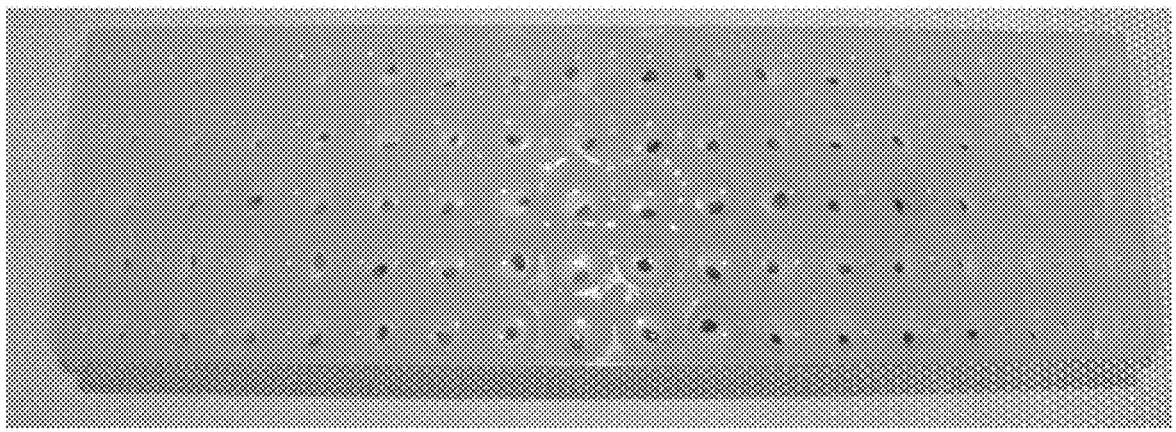
FIG. 8C shows an exemplary tray of RAP where UDMSO was replaced with two-parts 4 M NaOH.
Figure 8D:
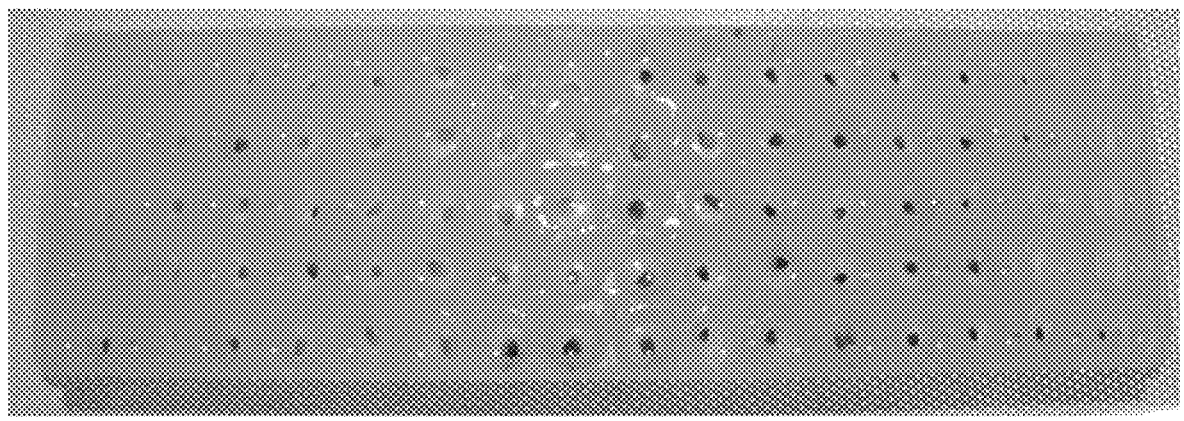
FIG. 8D shows an exemplary tray of RAP where UDMSO was replaced with equal parts 4 M NaOH and an extra volume water prior to heating.

Results:

Most of the sets were inconclusive. The first set returned no coloration (FIG. 8A). Most of the sodium hydroxide evaporated during the microwave step and too little remained for the reaction react. The second set had similar results to the first (FIG. 8B). Additionally, as shown in FIGS. 8C and 8D, increasing the amount of NaOH, adding water, or increasing the rest time to 10 minutes also did not produce any color and none of third (FIG. 8C), fourth, fifth (FIG. 8D), or sixth sets showed a color change.

Figure 8E:
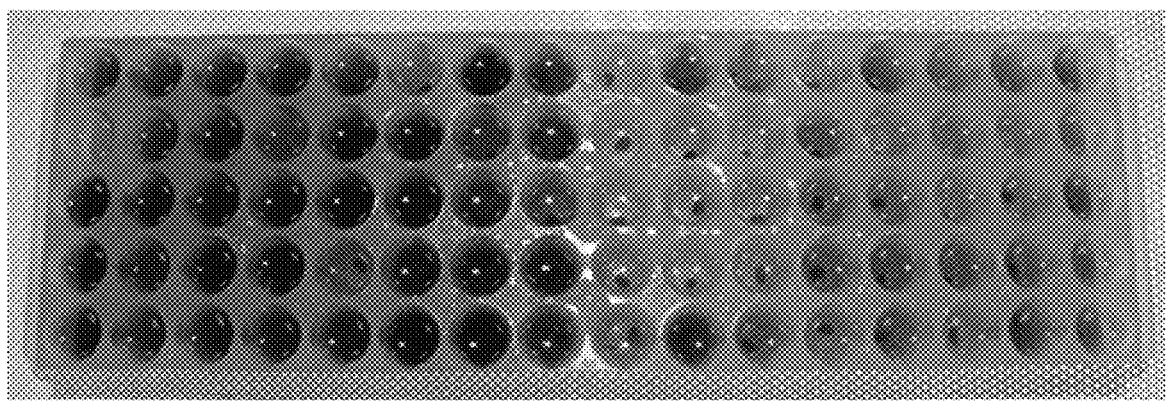
FIG. 8E shows an exemplary tray of RAP where UDMSO was replaced with equal part 4 M NaOH and a one-half part 85% lactic acid after microwaving.
Figure 8F:
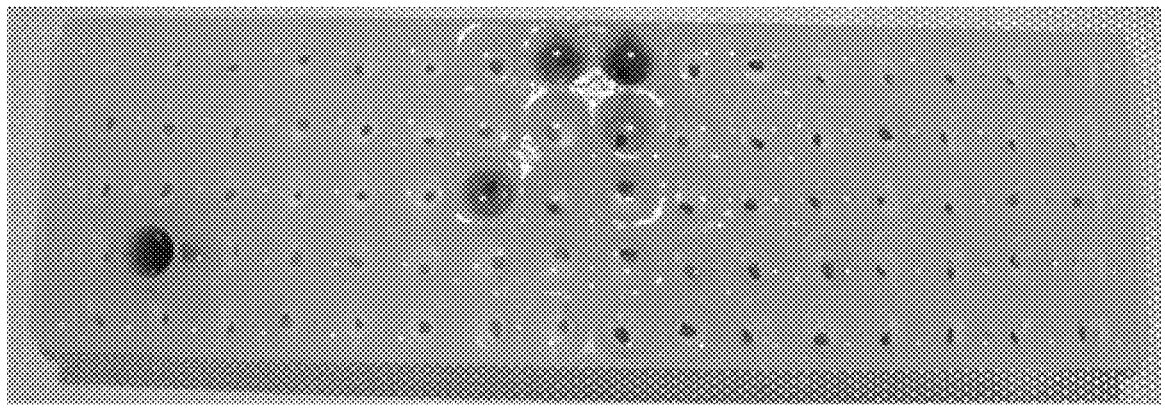
FIG. 8F shows an exemplary tray of RAP where UDMSO was replaced with two-parts 4 M NaOH and a one-half part 85% lactic acid after microwaving.
Figure 8G:
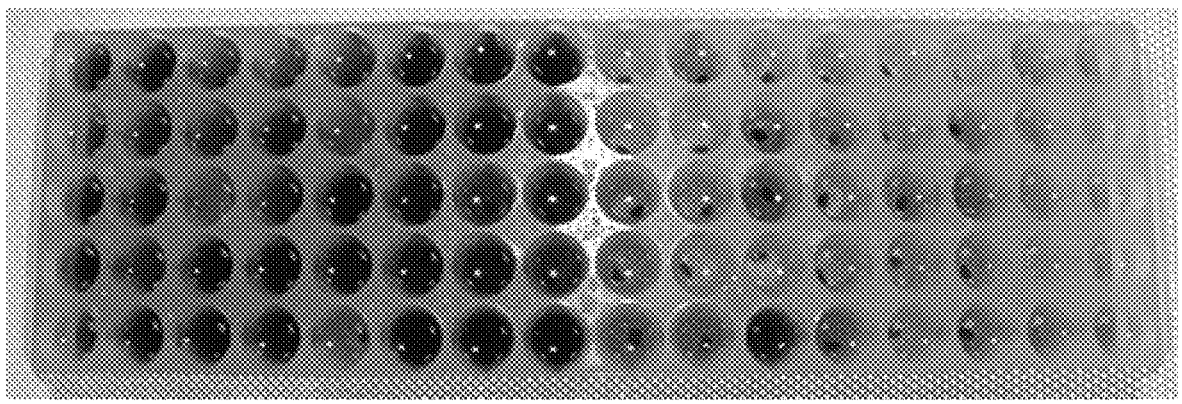
FIG. 8G shows an exemplary tray of RAP where UDMSO was replaced with one-half part 4 M NaOH and a one-half part 85% lactic acid before microwaving.

However, combing the lactic acid with the NaOH produced varied results. The seventh set had a different coloration of the samples: purple instead of blue (FIG. 8E). This method works, but coloration of faint high amylose detection fades slowly overtime and quickly once the sample is removed for microscopy. However, doubling the amount of NaOH in the eighth set resulted in almost no coloration (FIG. 8F). Reducing the amount of NaOH to be equal to the lactic acid in the ninth set resulted in a coloration and results as the standard RAP method, providing an alternate method to the standard REP method (FIG. 8G).

Figure 8H:
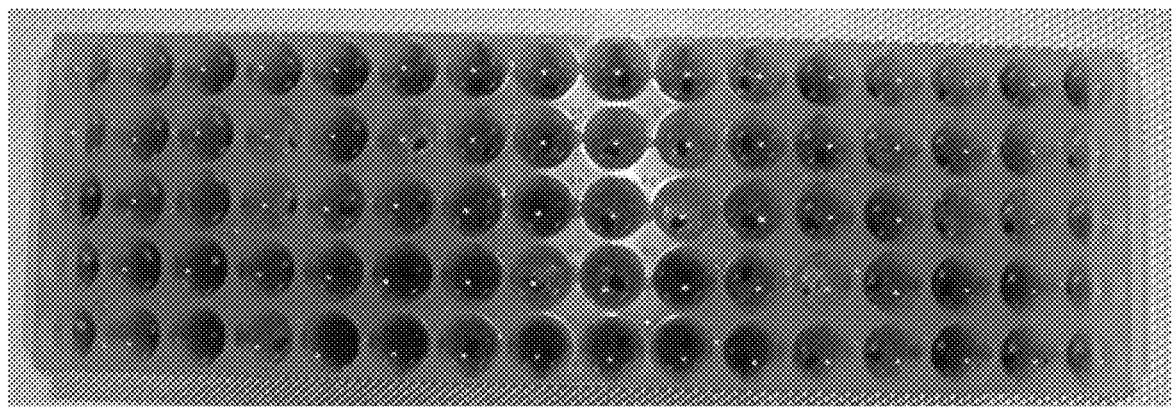
FIG. 8H shows an exemplary tray of RAP where UDMSO was replaced with equal part 4 M NaOH, allowing a 5-minute incubation, then adding a one-half part 85% lactic acid with no heating.

The $10^{th}$ set, however, shows that even this alternate method does not work without head (FIG. 8H). All samples turned light blue and there is no way to distinguish between the control and high amylose kernels.

Figure 8I:
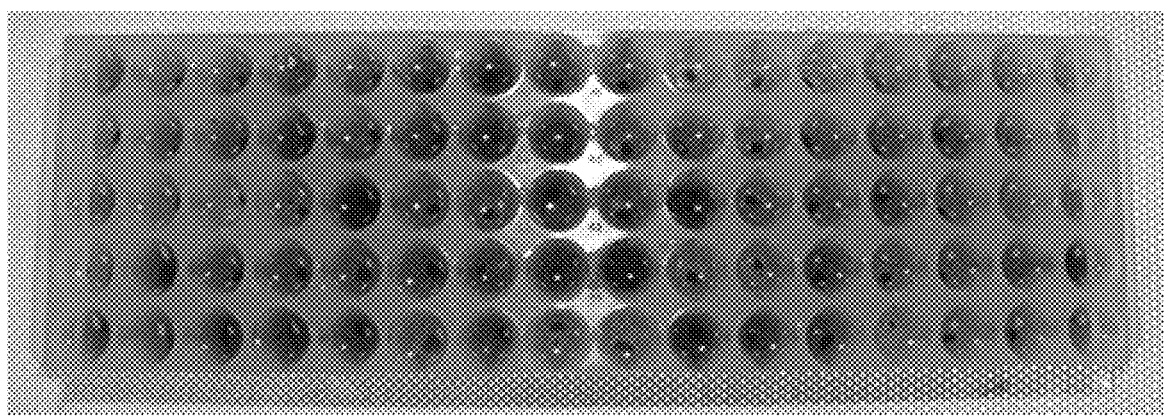
FIG. 8I shows an exemplary tray of RAP where UDMSO was replaced with two-parts 4 M NaOH and after a 5-minute incubation adding a one-half part 85% lactic acid.
Figure 8J:
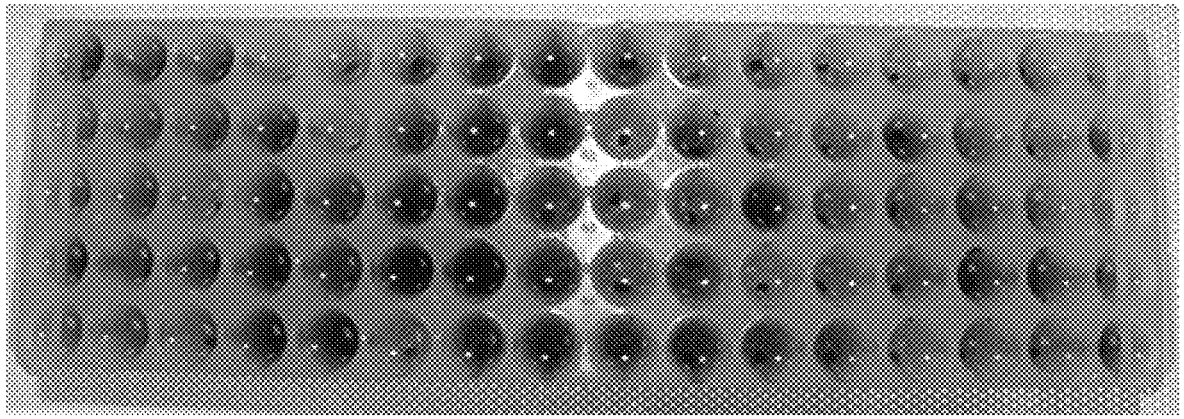
FIG. 8J shows an exemplary tray of RAP where UDMSO was replaced with 1.5-parts 4 M NaOH and after a 5-minute incubation a one-half part 85% lactic acid.
Figure 8K:
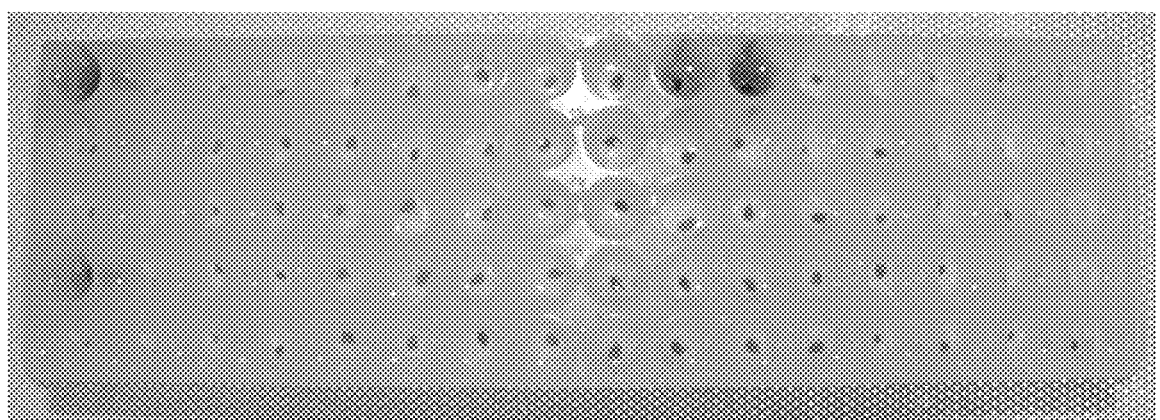
FIG. 8K shows an exemplary tray of RAP where UDMSO was replaced with 1.5-parts 4 M NaOH and after a 5-minute incubation a one part 85% lactic acid.
Figure 8L:
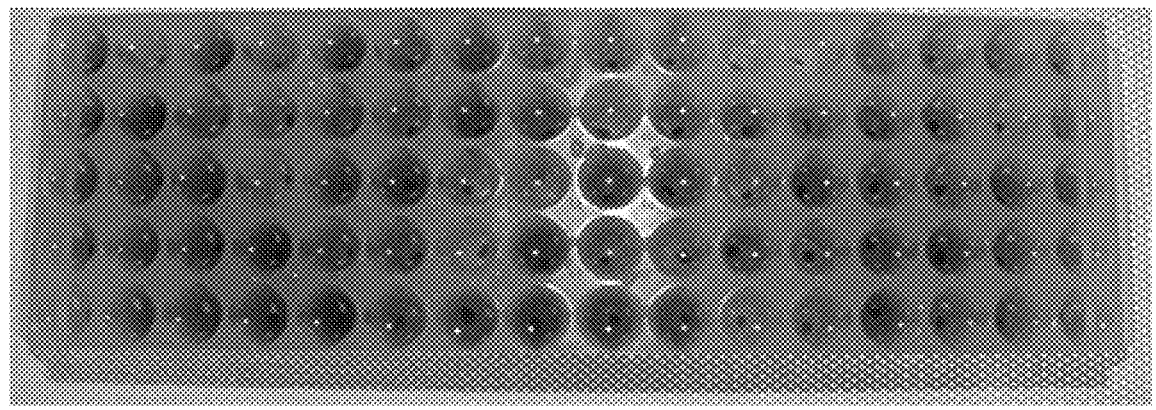
FIG. 8L shows an exemplary try of RAP where UDMSO was replaced with 1.5 parts 4 M NaOH and after a 5-minute incubation a x part 85% lactic acid.

Similarly, none of the $11^{th}$ through $14^{th}$ sets provided a good method. The $11^{th}$ set showed no differentiation in coloration (FIG. 8I), the $12^{th}$ set, while having better coloration, was still not defined enough to tell most of the high amylose samples (FIG. 8J), the $13^{th}$ set resulted in no coloration (FIG. 8K), and the $14^{th}$ set resulted in all blue samples (FIG. 8L).

Therefore, while a strong base can be used instead of UDMSO, it should be neutralized with an acid after heating.

| Sixth Set: | |
| --- | --- |
| QN0000524 HS253 | Generic Winter Wheat |
| 4/40 | 40/40 |
| 90% Pure | 0% Pure |

| Eighth Set | |
| --- | --- |
| QN0000524 HS253 | Generic Winter Wheat |
| 3/40 | 40/40 |
| 92.5% Pure | 0% Pure |

Example 10

Use of Strong Acid in Place of UDMSO

To see if a strong acid may replace UDMSO, hydrochloric acid (HCl) was exchanged with the UDMSO. Unless otherwise stated, all other parameters of the standard RAP procedure were used.

A first set replaced the UDMSO with equal parts 12 M HCl and followed the standard RAP procedure.

A second set replaced the UDMSO with equal parts 1 M HCl.

A third set replaced the UDMSO with equal parts 1 M HCl, but reduced the heating time by half to 30 seconds.

A fourth set replaced the UDMSO with equal parts 0.5 M HCl and used the shorted second heating time of the third set.

A fifth set reduced the heating even further to 10 seconds in 0.5 M HCl in equal parts to the UDMSO.

A sixth set used 0.5 M HCl in equal parts to the UDMSO and heated for 20 seconds.

A seventh set used 2 M HCl in equal parts to the UDMSO for 20 seconds.

An eighth set used 12 M HCl in equal parts to the UDMSO, but did not heat, allowed to incubate at room temp for 5 minutes before $KI_2$ addition.

A ninth set followed the procedure of the eighth set but with a one-half part of 12 M HCL to UDMSO.

A $10^{th}$ set followed the procedure of the eighth set but with an equal part of 1 M HCL to UDMSO.

An $11^{th}$ set added an equal part of 1M HCl, rested for five minutes, then added 1 part of 4M NaOH, rest for five more minutes, then added $KI_2$ and distilled water. A $12^{th}$ set set added an equal part of 3 M HCl, rested for five minutes, then added $KI_2$ and distilled water.

Sample: QN0000524 HS253, Generic Winter Wheat.
Reagents: 12 M and 1 M HCl, 4 m NaOH, $KI_2$, Distilled Water. All sets were run on a single tray of 40 half kernels per sample except for the $10^{th}$ set which used 8 half kernels per sample.

Results

Figure 9A:
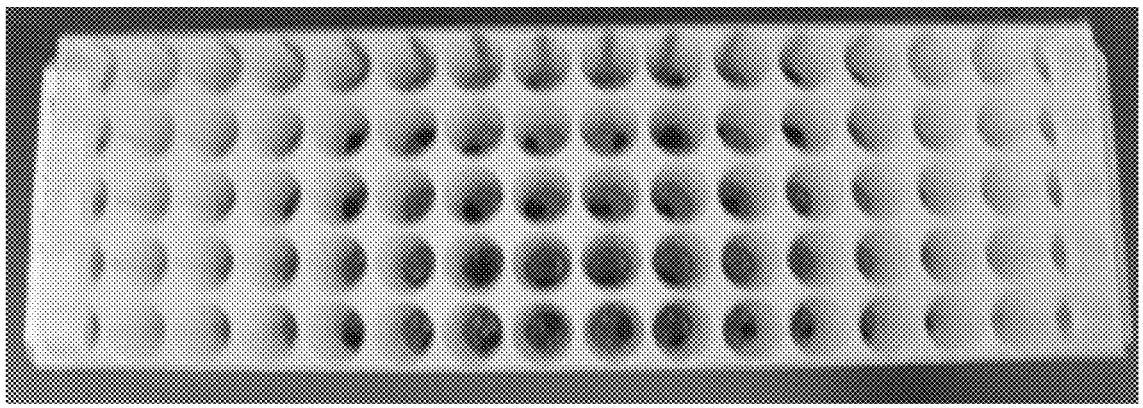
FIG. 9A shows an exemplary tray of RAP replacing UDMSO with an equal part 12 M HCl.
Figure 9B:
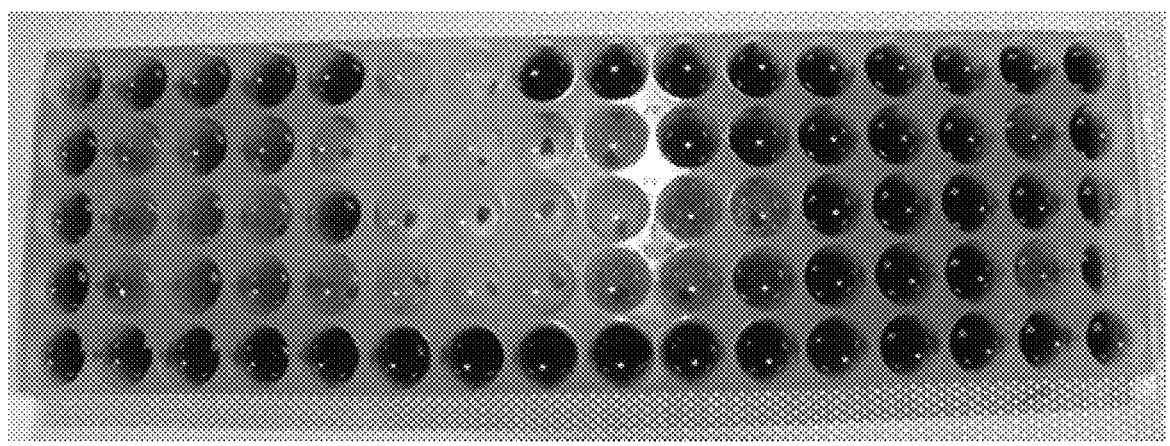
FIG. 9B shows an exemplary tray of RAP replacing UDMSO with an equal part 1 M HCl.

All the sets showed inconclusive results. The first set resulted in charred kernel and the release of heavy fumes so the test could not be run (FIG. 9A). The second test reduced the concentration of the acid to prevent the fumes and charring. However, as seen in FIG. 9B, this resulted in inconsistent coloration.

Figure 9C:
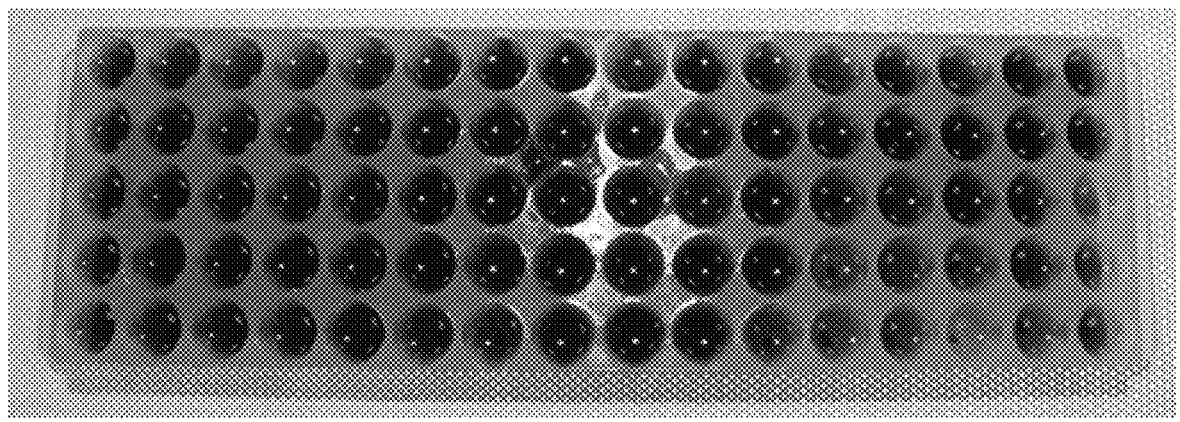
FIG. 9C shows an exemplary tray of RAP replacing UDMSO with an equal part 0.5 M HCl and a shortened 30 second heating.
Figure 9D:
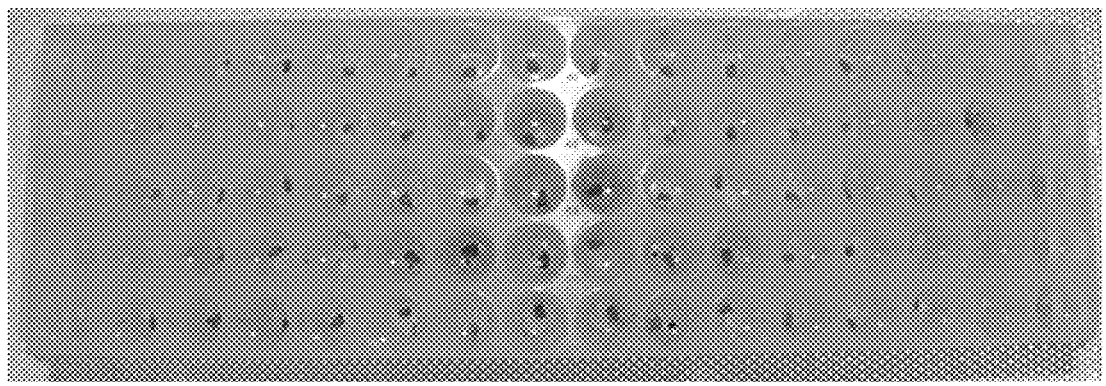
FIG. 9D shows an exemplary tray of RAP replacing UDMSO with an equal part 0.5 M HCl and a shortened 10 second heating.
Figure 9E:
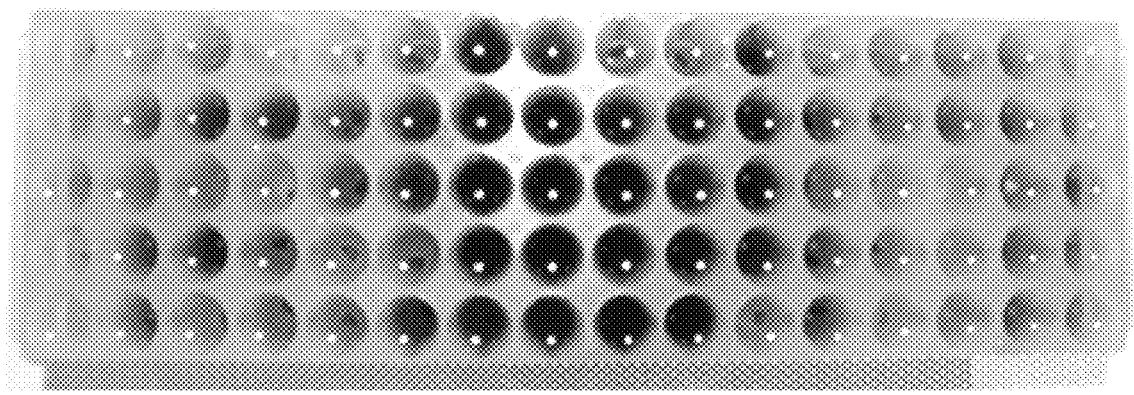
FIG. 9E shows an exemplary tray of RAP replacing UDMSO with an equal part 0.5 M HCl and a shortened 20 second heating.
Figure 9F:
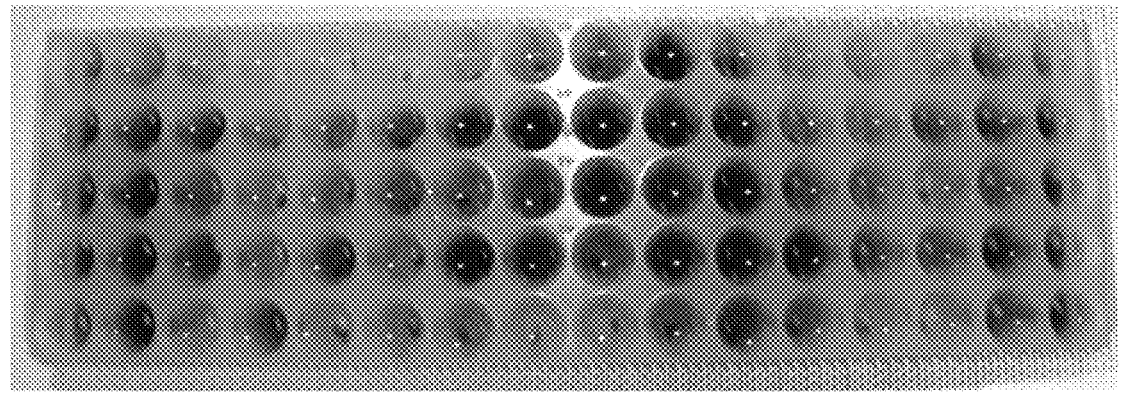
FIG. 9F shows an exemplary tray of RAP replacing UDMSO with an equal part 2 M HCl and a shortened 20 second heating.

To determine if this was an issue of an interaction between the concentration of the acid and the amount of heating time, the third through seventh sets altered the concentration of acid and/or the time spent in the microwave. Reducing the heating to 30 seconds and using either 1M HCl (third set) or 0.5 M HCl (fourth set, FIG. 9C) resulted in all blue samples. Reducing the time to 10 seconds (fifth set, FIG. 9D) resulted in no coloration, while 20 seconds resulted in an inconsistent coloration (sixth set, FIG. 9E). Increasing the concentration of acid back to 2 M, in the seventh set, still resulted in inconsistent coloration (FIG. 9F).

Figure 9G:
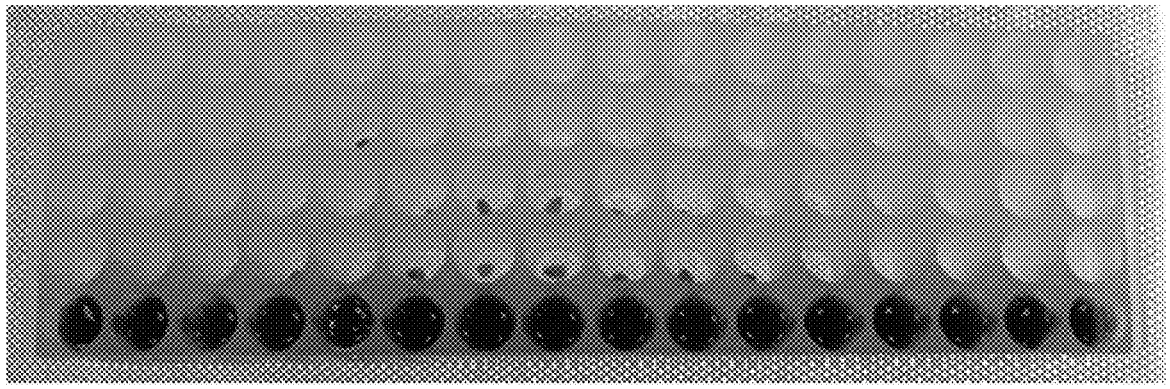
FIG. 9G shows an exemplary tray of RAP replacing UDMSO with an equal part 12 M HCl and a 5-minute incubation without heating.
Figure 9H:
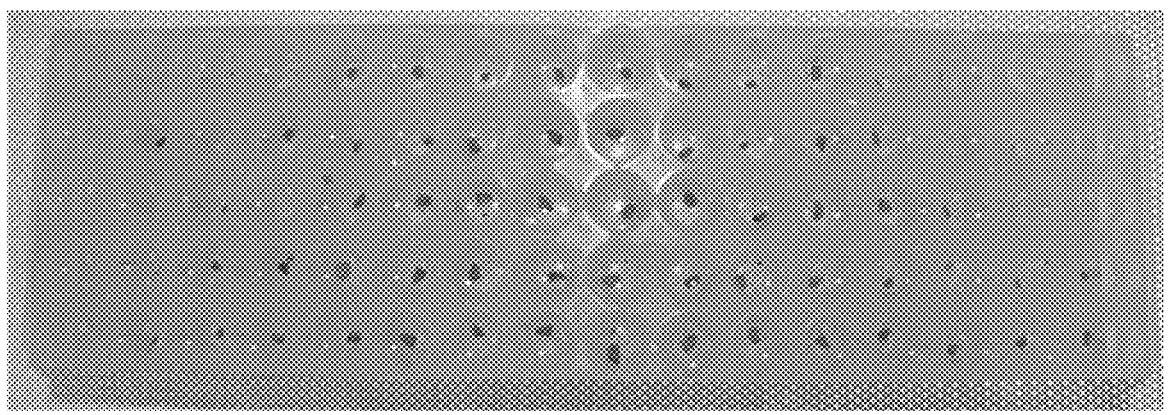
FIG. 9H shows an exemplary tray of RAP replacing UDMSO with an equal part 1 M HCl and a 5-minute incubation without heating.
Figure 9I:
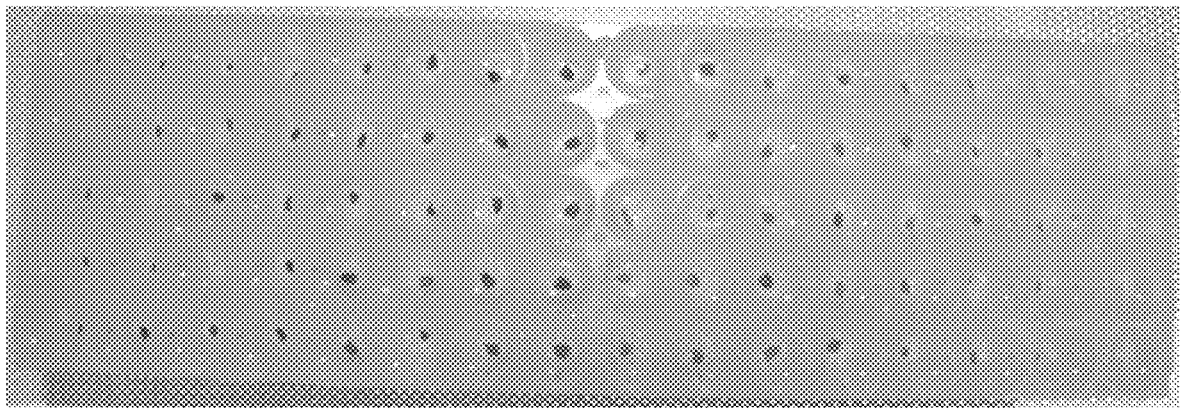
FIG. 9I shows an exemplary tray of RAP replacing UDMSO with an equal part 12 M HCl and a 5-minute incubation followed by equal part 4 M NaOH without heating.

Even without using the microwave for heating and allowing for room temperature incubation resulted in either all samples turning blue or no coloration. At high acid concentrations, 12 M HCl, at either one-part (eighth set) or one-half part (ninth set, FIG. 9G) UDMSO, all the samples turned blue. However, at lower concentrations (1 M, $10^{th}$ set, FIG. 9H or 3 M, $12^{th}$ set) or partially neutralized with NaOH, there was no coloration ($11^{th}$ set, FIG. 9I).

As both extremes were able to be achieved, either no color or all samples turning blue, one skilled in the art would expect to be able to optimize between the kernel preparation, heating, and/or reagent concentrations to produce a workable test.

Example 11

Figure 10A:
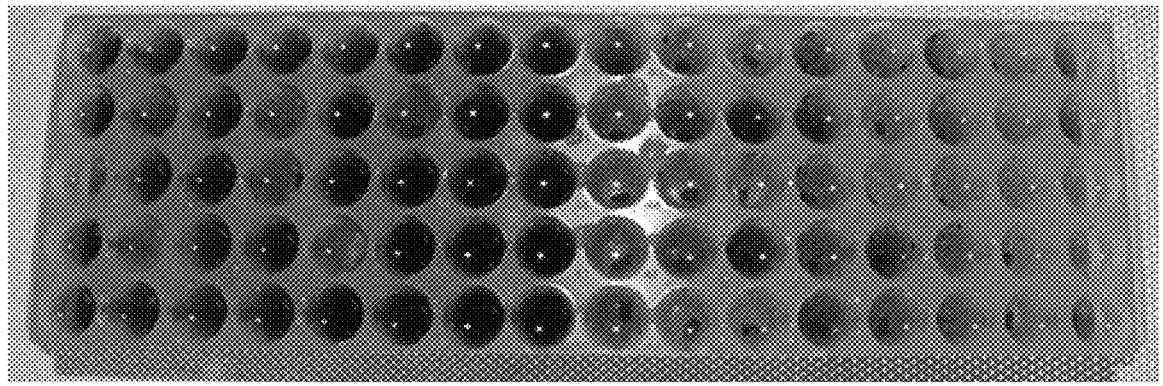
FIG. 10A shows an exemplary tray using standard RAP.
Figure 10B:
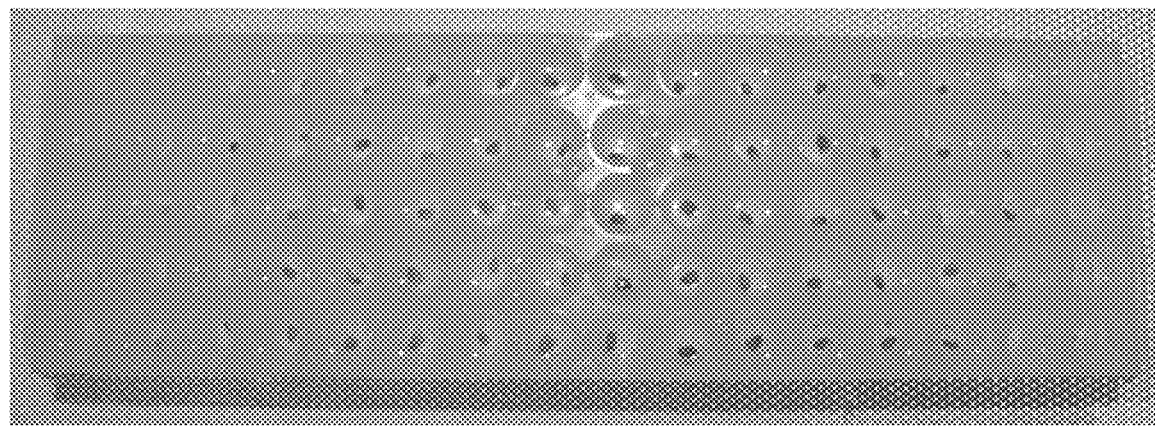
FIG. 10B shows an exemplary tray of RAP replacing $KI_2$ with an equal part KI.

To determine if $KI_2$ is needed instead of any iodide source, this Example used the standard RAP procedure but replaced Potassium Iodide Iodine ($KI_2$) with equal parts Potassium Iodide (KI).
Sample: QN0000524 HS253, Generic Winter Wheat. One tray was used with 40 half kernels of each variety.
Reagents: Urea-Dimethyl Sulfoxide (UDMSO), Potassium Iodide (KI), Distilled Water.
Results Test tray had no coloration (FIG. 10B) when compared to a control using $KI_2$ (FIG. 10A). The samples stayed clear as if only water had been added.

Example 12

To further determine if $KI_2$ is needed, this Example used the standard RAP but replaced $KI_2$ with equal parts iodide.
Sample: QN0000524 HS253, Generic Winter Wheat. One tray was used with 40 half kernels of each variety.
Reagents: Urea-Dimethyl Sulfoxide (UDMSO), Iodine (0.1 g of Iodine dissolved in 345 mL of Distilled Water, Distilled Water.

Results

Figure 11A:
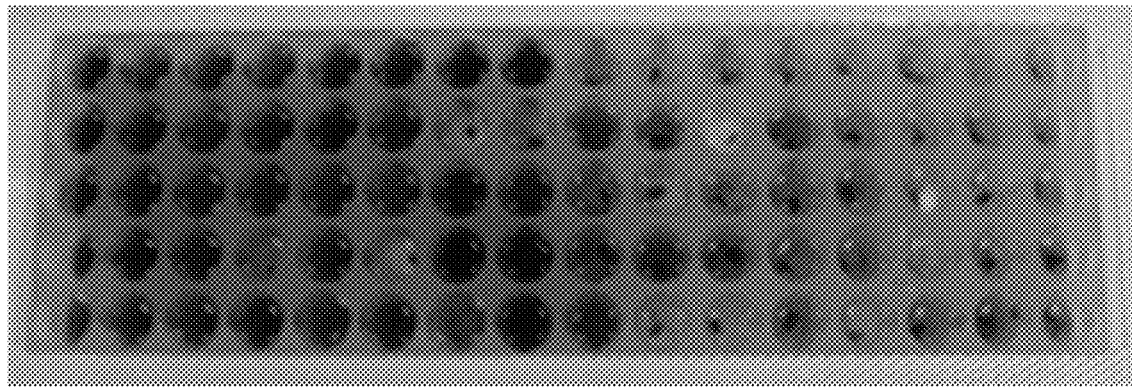
FIG. 11A shows an exemplary tray using standard RAP.
Figure 11B:
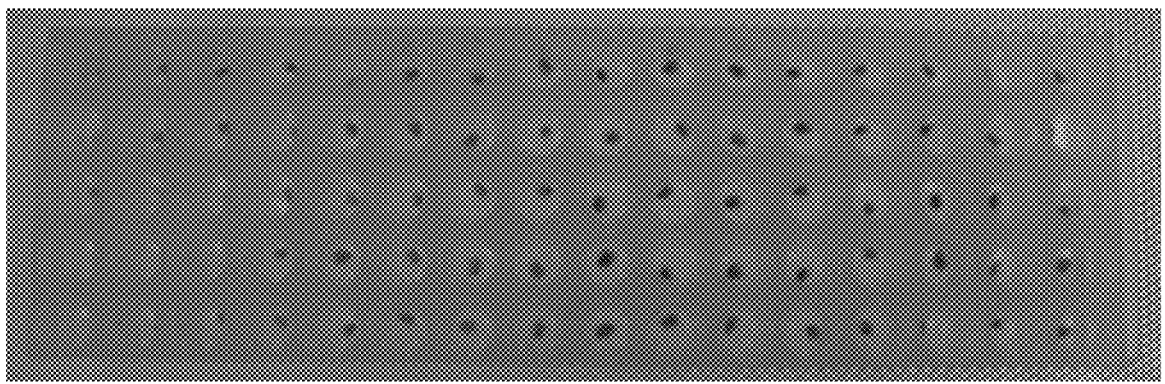
FIG. 11B shows an exemplary tray of RAP replacing $KI_2$ with an equal part iodine.

Test tray had no coloration (FIG. 11B) when compared to a control using KI$_2$ (FIG. 11A). Iodine concentration is too low for the sample to generate color. Addition of four times as much Iodine did not give sufficient coloration either.

Example 13

Altering Cooling Time

The standard RAP was run, with a change in the cooling time from 5 minutes to 0 minutes or 2.5 minutes after microwaving.
Sample: QN0000524 HS253, Generic Winter Wheat. Each test was performed on one tray with 40 half kernels from each sample.
Reagents: Urea-Dimethyl Sulfoxide (UDMSO), Distilled Water, Potassium Iodide Iodine (KI$_2$).
Results:

| 0 Minute Cooling | |
|---|---|
| QN0000524 HS253 | Generic Winter Wheat |
| 3/40 | 40/40 |
| 92.5% Pure | 0% Pure |

| 2.5 Minute Cooling | |
|---|---|
| QN0000524 HS253 | Generic Winter Wheat |
| 5/40 | 40/40 |
| 87.5% Pure | 0% Pure |

Figure 12A:
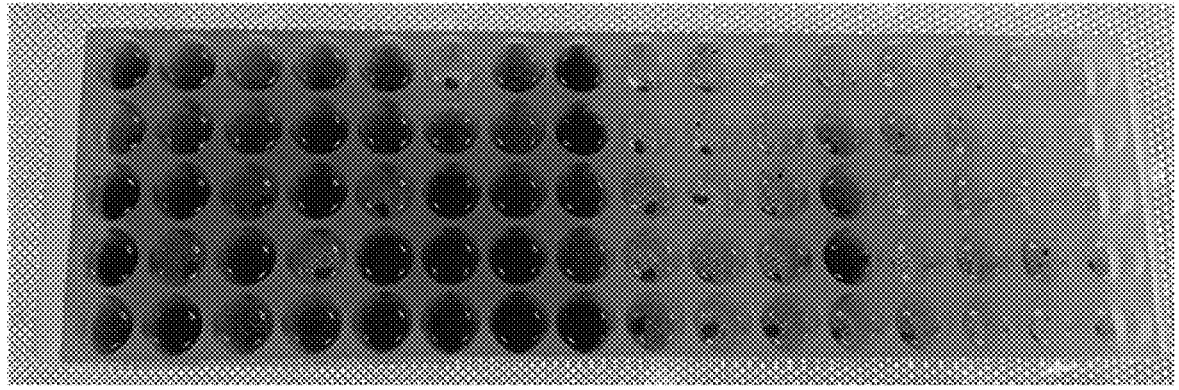
FIG. 12A shows an exemplary tray using RAP with a 0-minute cooldown.
Figure 12B:
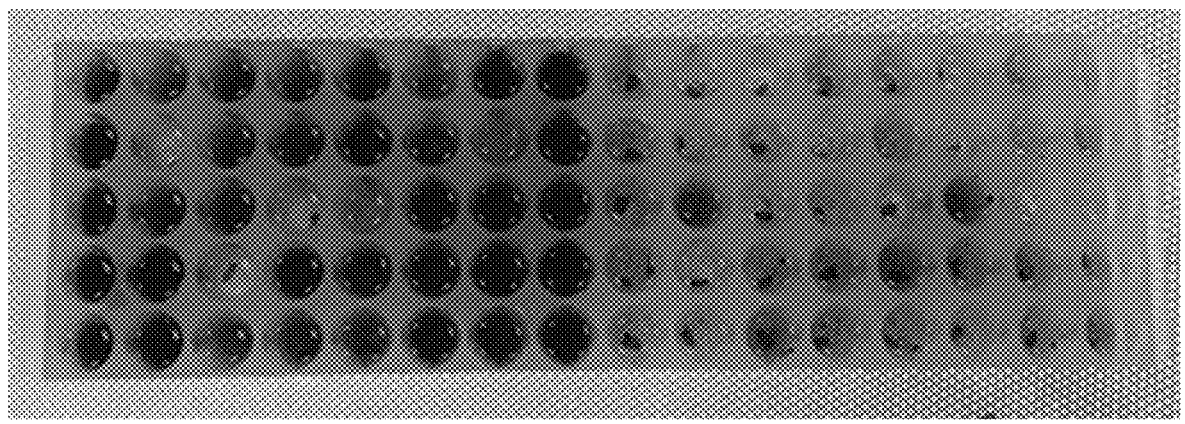
FIG. 12B shows an exemplary tray of RAP with a 2.5-minute cooldown.

Coloration after 0 minutes of cooling was not as clear as the standard RAP at first but still saturated enough to differentiate high and low amylose (FIG. 12A). Coloration improved at 2.5 minutes of cooling (FIG. 12B). This produced a usable method for a rapid amylose procedure.

Example 14

Exposure of Inner Kernel to Reagents

Figure 13A:
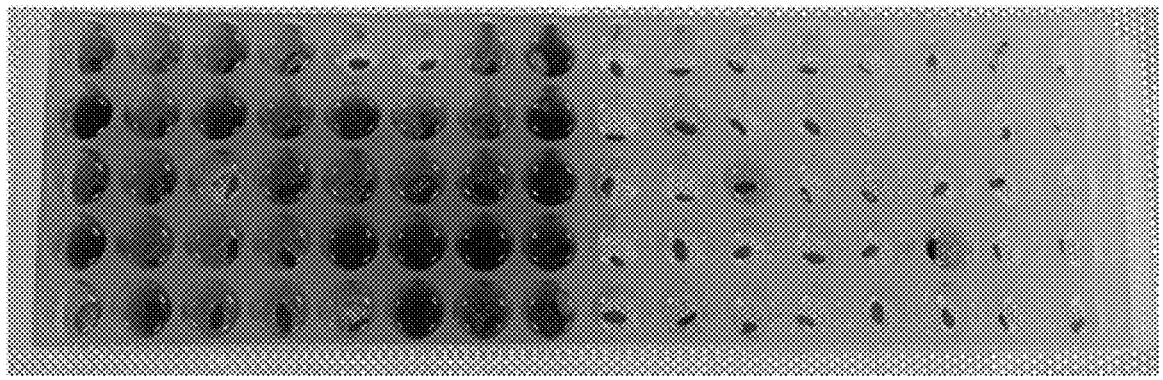
FIG. 13A shows an exemplary tray using RAP but leaving the kernel whole and intact.

In this experiment standard RAP was run except on different preparation of the kernel.
In a first set, the whole kernel was left whole.
In a second set, the half kernel was crushed after microwaving in UDMSO.
In a third set, the whole kernel was crushed prior to adding UDMSO.
In a fourth set, the half kernel was crushed prior to adding UDMSO.
Sample: QN0000524 HS253, Generic Winter Wheat. Each test was performed on one tray with 40 samples of each half kernel.
Chemicals: Urea-Dimethyl Sulfoxide (UDMSO), Distilled Water, Potassium Iodide Iodine (KI$_2$).
Results As shown in FIG. 13A, it is not possible to adequately differentiate the whole kernels. For the generic winter wheat, no coloration occurs as usual. However, the high amylose sample, QN0000524, turns hues of purple instead of blue with incomplete coloration. Therefore, most would have to be tested due to uncertainty making the test take too long to be considered rapid.

Figure 13B:
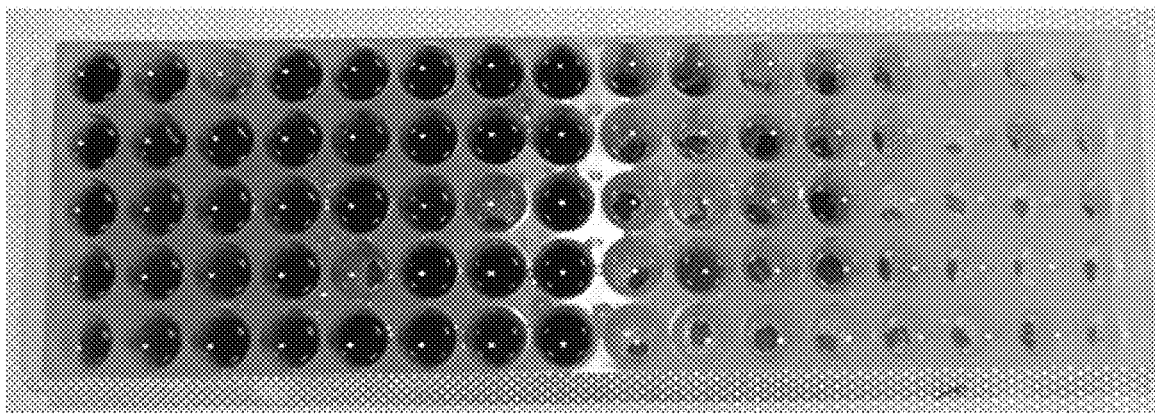
FIG. 13B shows an exemplary tray using RAP but crushing the half kernel after heating.
Figure 13C:
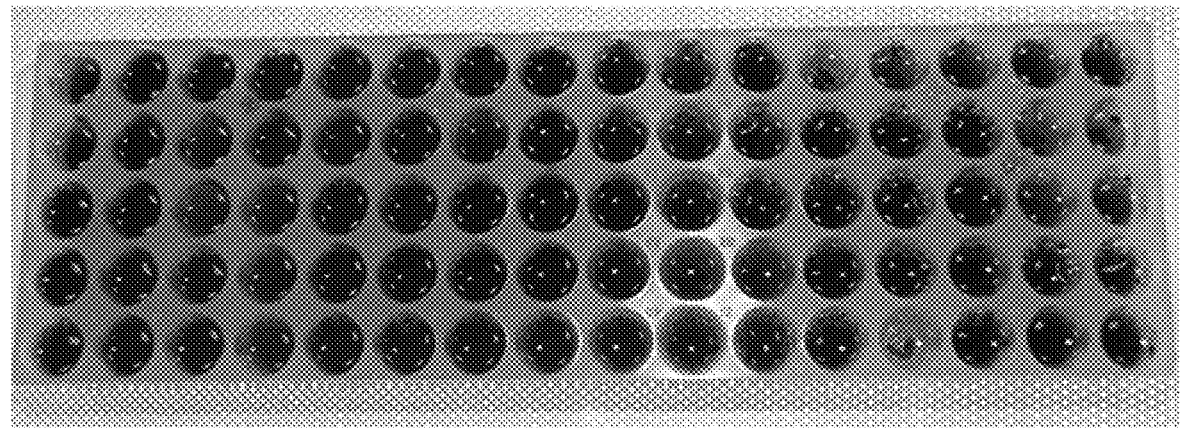
FIG. 13C shows an exemplary tray using RAP but crushing the whole kernel before adding UDMSO.
Figure 13D:
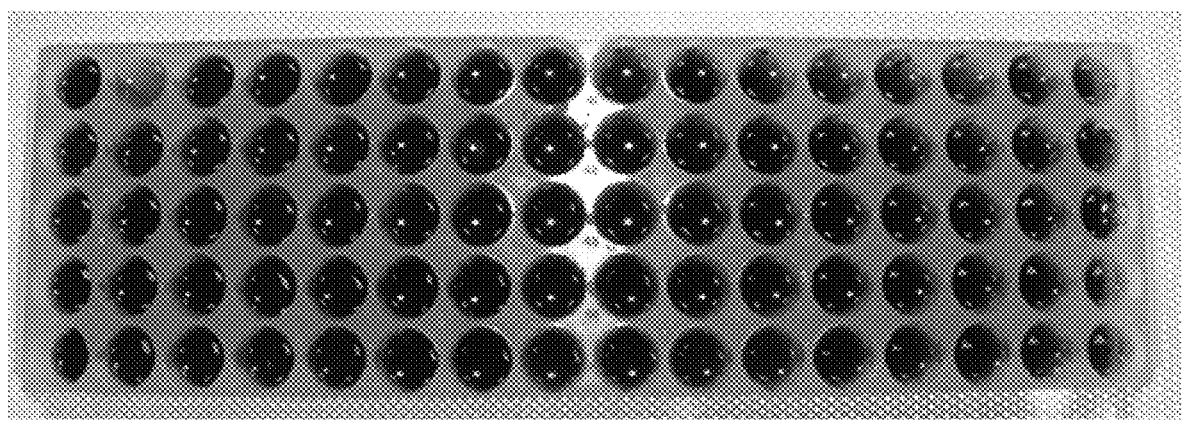
FIG. 13D shows an exemplary tray using RAP but crushing the half kernel before adding UDMSO.

However, crushing the kernels resulted in a blue color which was distinguishable from the low amylose winter wheat (FIG. 13B). Therefore, this is an alternative method for rapid detection if crushing does not cause cross contamination and is performed quickly. Crushing either the whole (FIG. 13C) or half (FIG. 13D) kernels at the start, before the addition of UDMSO, resulted in all the samples turning dark blue because too much starch is being activated by the reagents and each sample registers as high amylose due to the amount of starch released.

| Crushed Half Kernels | |
|---|---|
| QN0000524 HS253 | Generic Winter Wheat |
| 3/40 | 40/40 |
| 92.5% Pure | 0% Pure |

Example 15

Alternative Strong Bases in Place of UDMSO

Figure 14A:
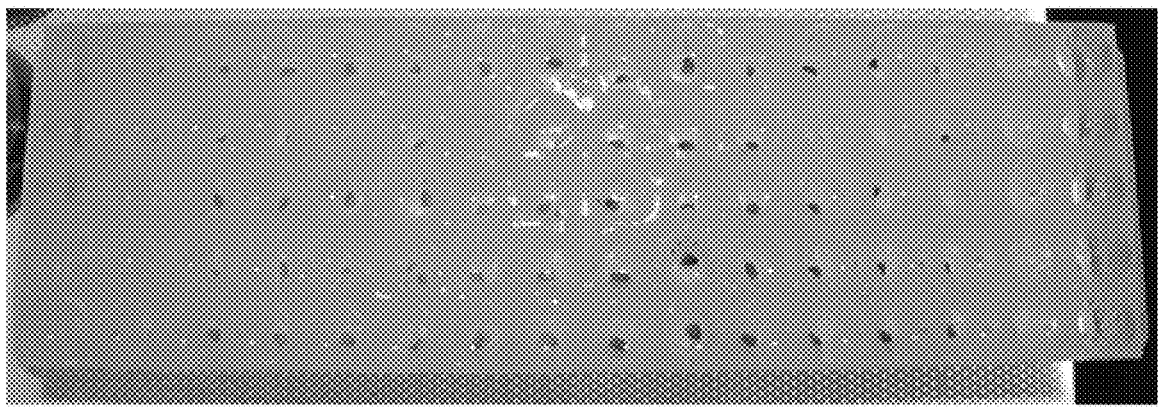
FIG. 14A shows an exemplary tray using RAP but replacing UDMSO with an equal part 2 M KOH.
Figure 14B:
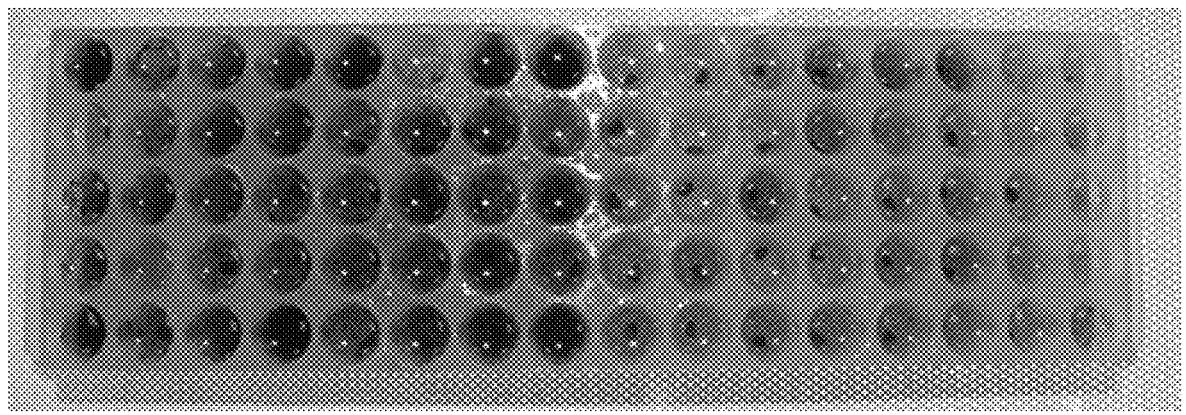
FIG. 14B shows an exemplary tray using RAP but replacing UDMSO with a one-half part 2 M KOH and after heating adding a one-half part 85% lactic acid.
Figure 14C:
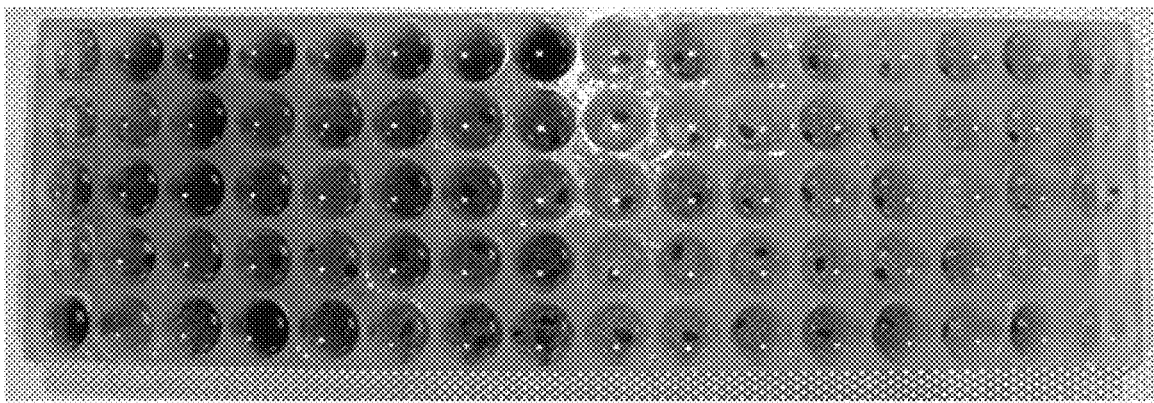
FIG. 14C shows an exemplary tray using RAP but replacing UDMSO with a one-half part 2 M KOH and after heating adding an equal part 85% lactic acid.

As NaOH may be used as alternative to UDMSO, KOH was also investigated to see if additional strong bases may be used. All RAP parameters were followed except for what is mentioned for each test set.
A first set replaced UDMSO with an equal part of 2 M KOH.
A second set doubled the amount of 2 M KOH.
A third set replaced UDMSO with equal part 2 M KOH and samples were allowed to sit for up to 15 minutes without heating.
A fourth set replaced UDMSO with a one-half part 2 M KOH and after heating added a one-half part 85% lactic acid.
A fifth set replicated the fourth set but with one part 85% lactic acid.
A sixth set did not microwave, but replaced UDMSO with one-half part 2 M KOH, allowed to rest for 5 minutes before adding one-half part 85% lactic acid and allowed to rest for 5 minutes.
A seventh set replicated the sixth set but with one-part 2 M KOH and one-part 85% lactic acid.
An eighth set replicated the sixth set with one-part 2 M KOH.
A ninth set replicated the sixth set with 1.5 parts 2 M KOH.
Sample: QN0000524 HS253, Generic Winter Wheat. Each test set was run in one tray with 40 samples of each variety in as a half kernel.
Reagents: Potassium Hydroxide (KOH) 2M, Distilled Water, KI$_2$, 85% lactic acid.
Results Like NaOH, KOH alone is not sufficient to detect amylose in a sample. None of the first, second, or third sets produce any coloration (FIG. 14A). However, the addition of 85% lactic acid does produce coloration. The fourth (FIG. 14B) and fifth (FIG. 14C) sets were both able to coloration, however, the fourth set does not differentiate between high and low amylose well enough and microscopy would have to be used for far too many to consider this method achieve an acceptable speed. Similarly, the fifth set produces a thin purple material comes off the high amylose samples which helps identify which ones are high amylose, along with color changes. While this method works, distinction of high amylose sample may require too much microscopy to also be considered a rapid test.

| Fourth Set | |
|---|---|
| QN0000524 HS253 | Generic Winter Wheat |
| 3/40 92.5% Pure | 40/40 0% Pure |

| Fifth Set | |
|---|---|
| QN0000524 HS253 | Generic Winter Wheat |
| 2/40 95% Pure | 40/40 0% Pure |

Figure 14D:
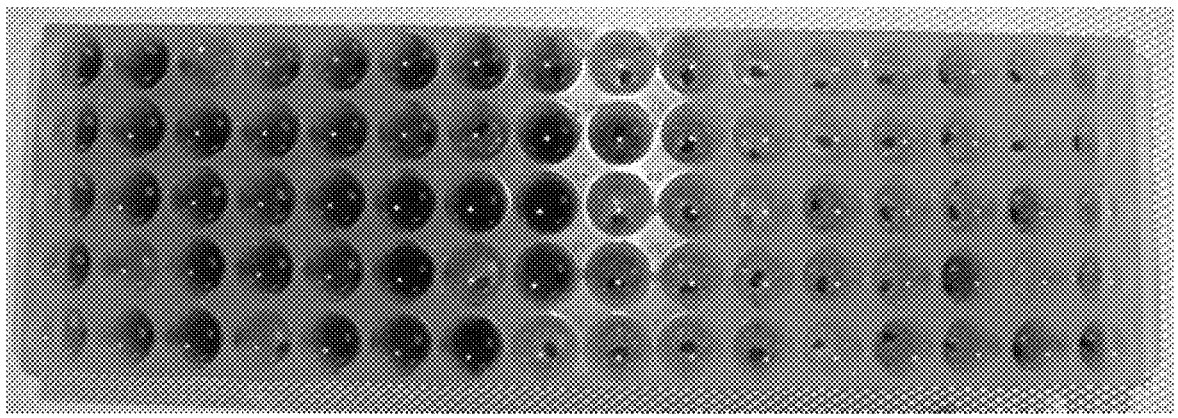
FIG. 14D shows an exemplary tray using RAP but replacing UDMSO with a one-half part 2 M KOH and after a 5-minute incubation and no heating adding a one-half part 85% lactic acid.
Figure 14E:
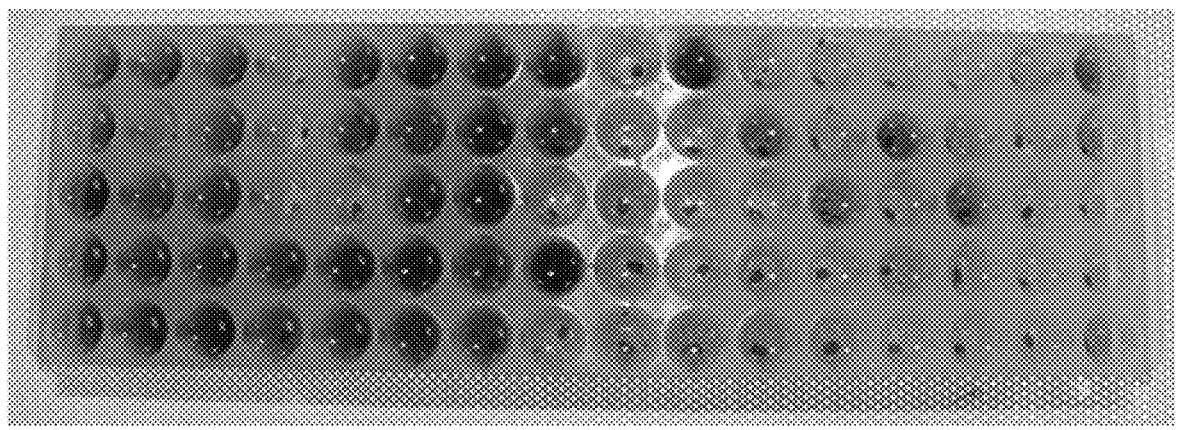
FIG. 14E shows an exemplary tray using RAP but replacing UDMSO with a one-half part 2 M KOH and after a 5-minute incubation and no heating adding a one-part 85% lactic acid.
Figure 14F:
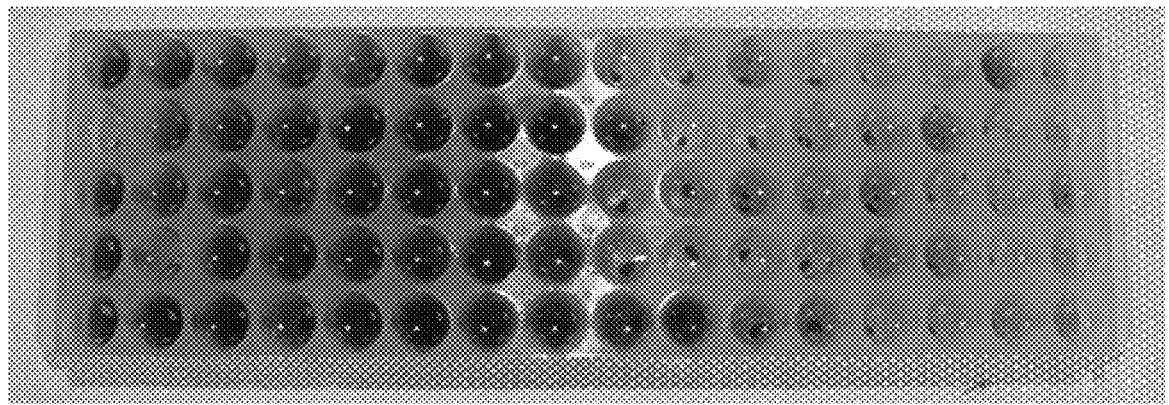
FIG. 14F shows an exemplary tray using RAP but replacing UDMSO with an one-part 2 M KOH and after a 5-minute incubation and no heating adding a one-half part 85% lactic acid.
Figure 14G:
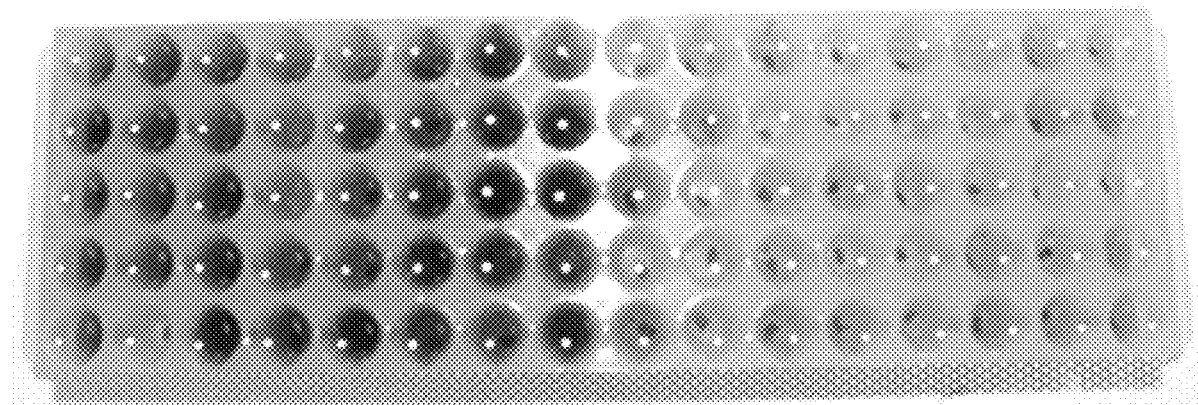
FIG. 14G shows an exemplary tray using RAP but replacing UDMSO with a 1.5-part 2 M KOH and after a 5-minute incubation and no heating adding a one-half part 85% lactic acid.

In contrast, KOH without heating does produce a reliable and rapid test. Starting from the sixth set (FIG. 14D) and increasing to the eighth set (FIG. 14F) improves the rapid detection of high amylose samples, with the seventh set (FIG. 14E) being intermediate. However, further increases in KOH reduces the quality of the coloration (ninth set, FIG. 14G) and appears similar to the intermediate results of the seventh set.

Therefore, like NaOH, KOH may replace UDMSO as in the RAP when combined with an acid. Unlike NaOH, KOH does not need to be heated and could be useful for field research when a heating unit is not available. Other strong bases would be expected to be able to work as well.

| Sixth Set | |
|---|---|
| QN0000524 HS253 | Generic Winter Wheat |
| 6/40 85% Pure | 40/40 0% Pure |

| Seventh Set | |
|---|---|
| QN0000524 HS253 | Generic Winter Wheat |
| 7/40 82.5% Pure | 40/40 0% Pure |

| Eighth Set | |
|---|---|
| QN0000524 HS253 | Generic Winter Wheat |
| 2/40 95% Pure | 40/40 0% Pure |

Example 16

Use of RAP on Corn

To see if standard RAP may be used on corn, high amylose corn kernels were compared to generic cob corn. The kernels were cut different to expose different amounts to the solvents.

A first set cut the kernels the short way using the standard RAP method.

A second set cut the kernels the long way using the standard RAP method.

A third set cut the kernels in fourths using the standard RAP method.

A fourth set cut the kernels in fourths and swapping UDMSO with one-part 2 M KOH, allowed a 5-minute incubation, adding one-half part 85% lactic acid and allowing another 5-minute incubation.

A fifth set replicated the fourth set but used 1.5-part 2 M KOH.

A sixth set replicated the fourth set but used 1.5-part 2 M KOH and 1/10-part 85% lactic acid.

A seventh set replicated the fourth set but used 1.5-part 2 M KOH and 3/10-part 85% lactic acid.

An eighth set using a series of 1, 5, 10, 15, 20 and 25 mg of corn starch control.

A ninth set in which a rotary tool was used to remove the tip of the bran layer to expose the starch. Only 15 low amylose kernels were used for this set and using standard RAP.

A $10^{th}$ set in which a rotary tool was used to thin the bran layer without exposing the starch. 10 of each kernel was used for this set and using standard RAP.

Sample: High amylose Corn, generic Cob Corn. Unless otherwise stated above, a single tray using 40 half kernels of both varieties were used for each set.

Reagents: UDMSO, KOH 2 M, $KI_2$, Lactic Acid 85%, Distilled Water.

Results

Figure 15A:
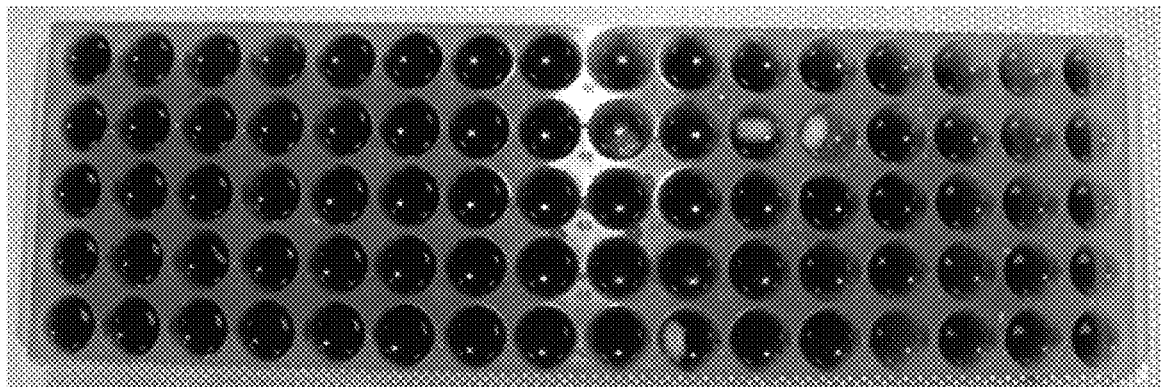
FIG. 15A shows an exemplary tray using RAP on a corn kernel cut the short way.
Figure 15B:
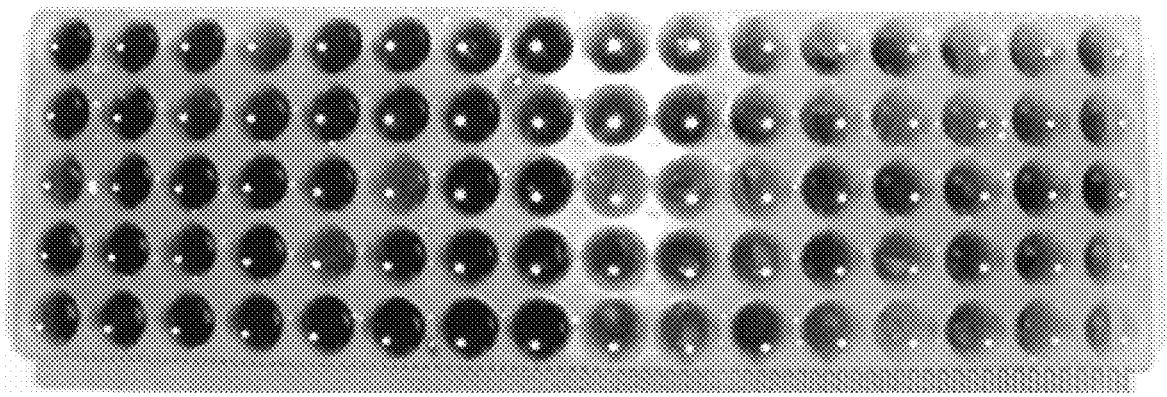
FIG. 15B shows an exemplary tray using RAP on a corn kernel cut the long way.
Figure 15C:
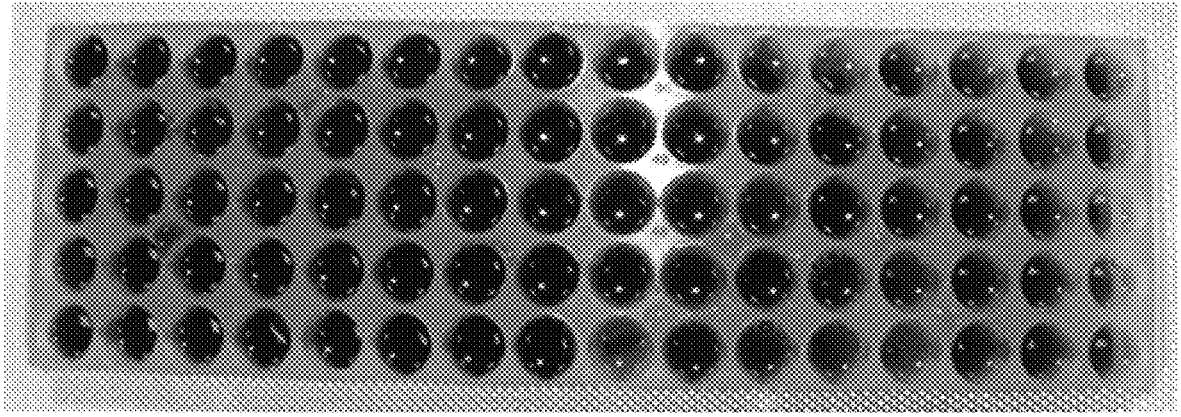
FIG. 15C shows an exemplary tray using RAP on a corn kernel into quarters.

Due to the high amylose content in a corn kernel, the first (FIG. 15A), second (FIG. 15B), and third (FIG. 15C) set all resulted in all samples during blue.

Figure 15D:
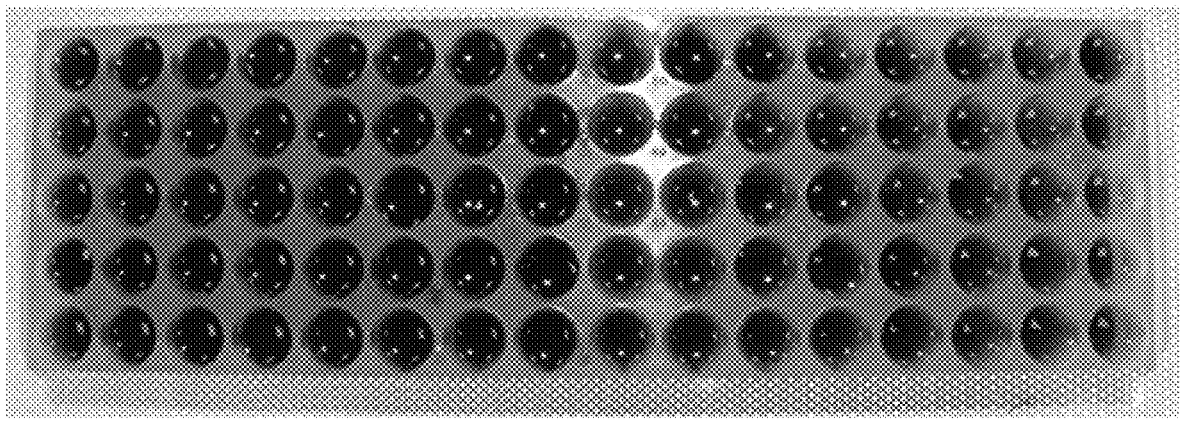
FIG. 15D shows an exemplary tray using the KOH variation of RAP with one-part KOH and one-half part 85% lactic acid.
Figure 15E:
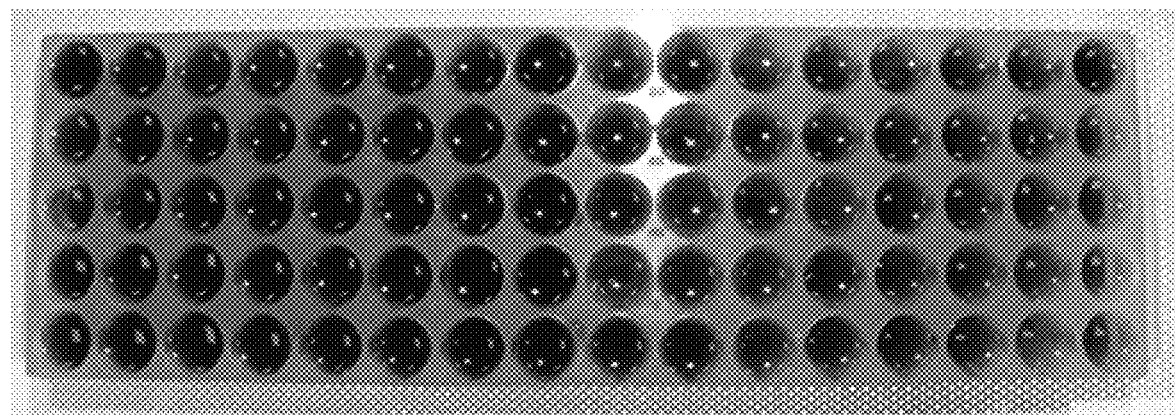
FIG. 15E shows an exemplary tray using the KOH variation of RAP with 1.5-part KOH and one-half part 85% lactic acid.
Figure 15F:
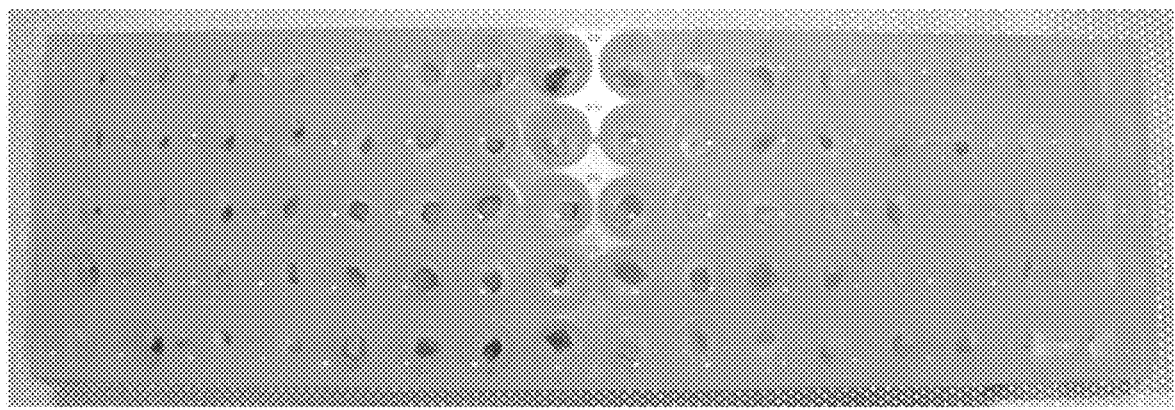
FIG. 15F shows an exemplary tray using the KOH variation of RAP with 1.5-part KOH and 1/10-part 85% lactic acid.
Figure 15G:
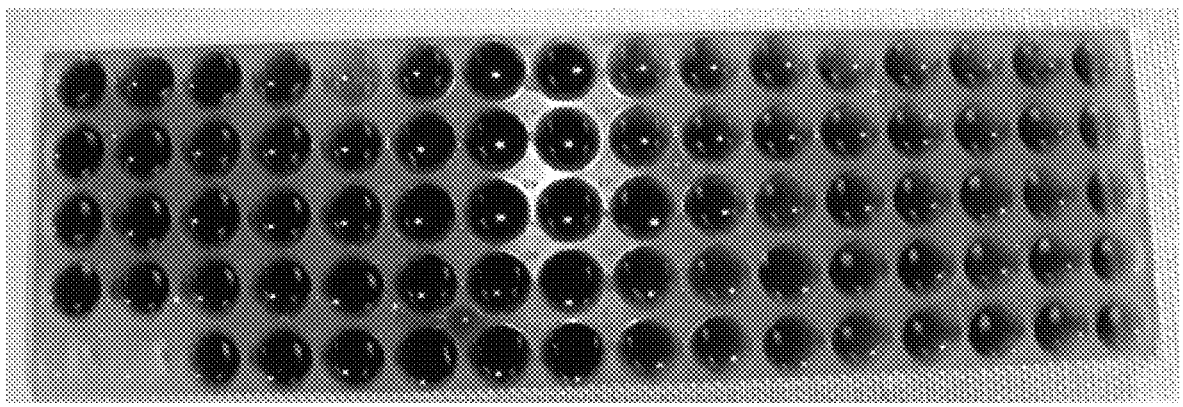
FIG. 15G shows an exemplary tray using the KOH variation of RAP with 1.5-part KOH and 3/10-half part 85% lactic acid.

Using the KOH version resulted in mixed results. The fourth (FIG. 15D) and fifth (FIG. 15E) sets both resulted in all kernels turning blue, with some detectable difference between the kernels in the fifth set. However, the sixth set (FIG. 15F) showed no coloration. The seventh set also resulted in all kernels turning blue (FIG. 15G).

Further, all the corn starch controls turned blue, down to 1 mg. Therefore, less than 1 mg of corn starch should be used for any method.

Figure 15H:
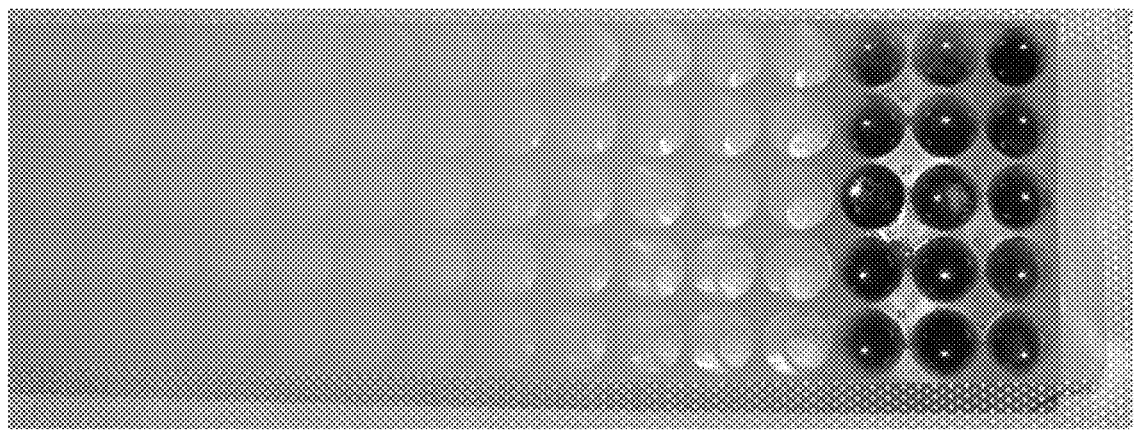
FIG. 15H shows an exemplary tray using standard RAP on low amylose wheat where the only the tip of the bran layer was removed to expose the starch.
Figure 15I:
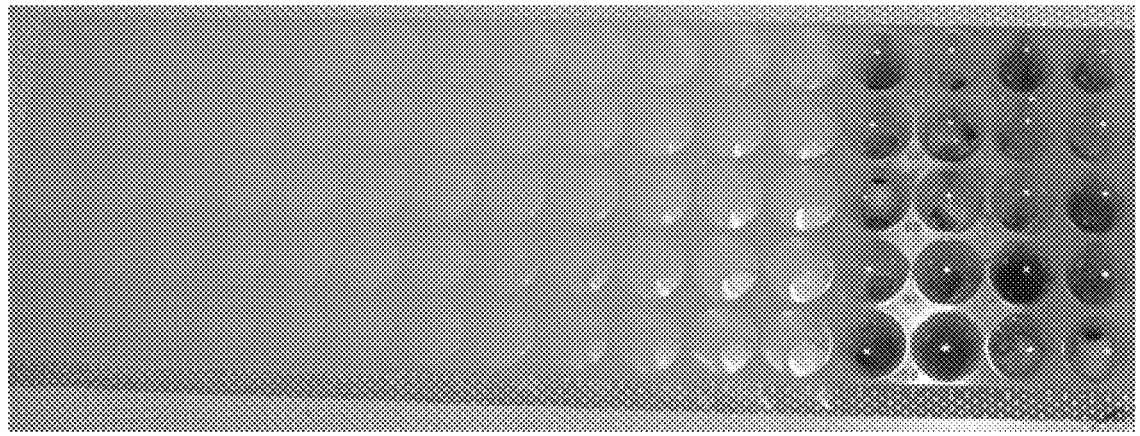
FIG. 15I shows an exemplary tray using standard RAP where the bran layer was thinned.

The rotary tool also resulted in indistinguishable results. As shown in FIG. 15H, all the samples produced an intermediate coloration when the bran layer was removed, but no coloration when the bran layer was thinned (FIG. 15I).

As both extremes were obtained, from no coloration to all samples turning blue, and an intermediate result (the fifth set), it is expected that one skilled in the art could optimize the reagents, along with a sufficiently small sample, to detect the difference in high amylose vs. normal amylose corn or other grain kernels.

While the invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of testing a quantity of seeds for amylose content comprising:
    obtaining a quantity of kernels;
    preparing the kernel by exposing the kernel starch, wherein the kernel starch is exposed without extraction from the kernel;
    applying a solvent to the starch;
    gelatinizing the amylose;
    applying a detection molecule; and
    detecting a color difference.

2. The method of claim 1, wherein the kernels are a cereal grain.

3. The method of claim 2, wherein the cereal grain is maize, corn, rice, soybean, wheat, rye, millet, sorghum, barley, oats, rice, spelt, teff, fonio, triticale, amaranth, buckwheat, chia, *quinoa*, legume, or oilseed.

4. The method of claim 2, wherein the cereal grain is wheat.

5. The method of claim 1, wherein exposing the kernel starch comprises cutting or crushing the kernel.

6. The method of claim 5, wherein the exposing the kernel starch is cutting.

7. The method of claim 6, wherein the kernel is cut in about half.

8. The method of claim 1, wherein the solvent is dimethyl sulfoxide, a strong base, a strong acid, or a halogen salt.

9. The method of claim 8, wherein the solvent is urea and dimethyl sulfoxide.

10. The method of claim 8, wherein the solvent is a strong base.

11. The method of claim 10, wherein the strong base is potassium hydroxide, sodium hydroxide, barium hydroxide, cesium hydroxide, strontium hydroxide, calcium hydroxide, lithium hydroxide, rubidium hydroxide, butyl lithium, lithium diisopropylamide, lithium diethylamide, sodium amide, sodium hydride, and lithium bis(trimethylsilyl)amide.

12. The method of claim 10, further comprising applying a neutralizing amount of an organic acid.

13. The method of claim 12, wherein the organic acid is lactic acid, acetic acid, glycolic acid, propionic acid, 3-hydroxypropanoic acid, malonic acid, butyric acid, or hydroxybutyric acid.

14. The method of claim 8, wherein the solvent is a strong acid.

15. The method of claim 14, wherein the strong acid is hydrochloric acid, nitric acid, sulfuric acid, hydrobromic acid, perchloric acid, or chloric acid.

16. The method of claim 8, wherein the solvent is a halogen salt.

17. The method of claim 16, wherein the halogen salt is calcium fluoride, calcium bromide, calcium chloride, calcium iodine beryllium chloride, magnesium chloride, strontium chloride, barium chloride, or radium chloride.

18. The method of claim 1, wherein gelatinizing the amylose further comprises applying electromagnetic radiation.

19. The method of claim 1, wherein gelatinizing does not apply electromagnetic radiation.

* * * * *